US012070489B2

(12) United States Patent
Shaked et al.

(10) Patent No.: US 12,070,489 B2
(45) Date of Patent: Aug. 27, 2024

(54) METHOD OF TREATING CANCER WITH A CANCER THERAPY IN COMBINATION WITH ANOTHER THERAPEUTIC AGENT

(71) Applicant: Rappaport Family Institute for Research in the Medical Sciences, Haifa (IL)

(72) Inventors: Yuval Shaked, Binyamina (IL); Ziv Raviv, Haifa (IL); Dror Yeger, Zichron Yaakov (IL)

(73) Assignee: Rappaport Family Institute for Research In the Medical Sciences, Haifa (IL)

( * ) Notice: Subject to any disclaimer, the term of this patent is extended or adjusted under 35 U.S.C. 154(b) by 224 days.

(21) Appl. No.: 16/712,800

(22) Filed: Dec. 12, 2019

(65) Prior Publication Data

US 2020/0190183 A1   Jun. 18, 2020

Related U.S. Application Data

(63) Continuation-in-part of application No. 16/218,177, filed on Dec. 12, 2018.

(51) Int. Cl.
| | | |
|---|---|---|
| *A61K 38/20* | (2006.01) | |
| *A61K 38/17* | (2006.01) | |
| *A61P 35/00* | (2006.01) | |
| *C07K 16/24* | (2006.01) | |
| *C07K 16/28* | (2006.01) | |
| *G01N 33/574* | (2006.01) | |
| *A61K 45/06* | (2006.01) | |
| *A61P 31/00* | (2006.01) | |

(52) U.S. Cl.
CPC ........ *A61K 38/2046* (2013.01); *A61K 38/177* (2013.01); *A61P 35/00* (2018.01); *C07K 16/248* (2013.01); *C07K 16/2866* (2013.01); *G01N 33/574* (2013.01); *A61K 45/06* (2013.01); *A61P 31/00* (2018.01)

(58) Field of Classification Search
None
See application file for complete search history.

(56) References Cited

U.S. PATENT DOCUMENTS

| | | | | |
|---|---|---|---|---|
| 5,595,756 A | * | 1/1997 | Bally | A61K 9/1272 |
| | | | | 264/4.1 |
| 11,155,614 B2 | * | 10/2021 | Shaked | G01N 33/53 |
| 2016/0024585 A1 | | 1/2016 | Nixon et al. | |
| 2017/0114125 A1 | | 4/2017 | Sabbadini et al. | |

FOREIGN PATENT DOCUMENTS

| | | |
|---|---|---|
| AU | 2016250478 A1 | 11/2016 |
| JP | 2011526674 A | 10/2011 |
| JP | 2015516806 A | 6/2015 |
| JP | 2016-520800 A | 7/2016 |
| JP | 2016535275 A | 11/2016 |
| JP | 2019503386 A | 2/2019 |
| JP | 2020525758 A | 8/2020 |
| WO | 2005119260 A2 | 12/2005 |
| WO | 2009032084 A1 | 3/2009 |
| WO | 2012151574 A1 | 11/2012 |
| WO | 2013106765 A1 | 7/2013 |
| WO | 2013148288 A1 | 10/2013 |
| WO | 2016156501 A1 | 10/2016 |
| WO | 2017011907 A1 | 1/2017 |
| WO | 2017024207 A1 | 2/2017 |
| WO | 2017040960 A1 | 3/2017 |
| WO | 2017091072 A1 | 6/2017 |
| WO | 2017132536 A1 | 8/2017 |
| WO | 2017140826 A1 | 8/2017 |
| WO | 2018071824 A1 | 4/2018 |
| WO | 2018104483 A1 | 6/2018 |
| WO | 2018222711 A2 | 12/2018 |
| WO | 2018225062 A1 | 12/2018 |
| WO | 2018225063 A1 | 12/2018 |

OTHER PUBLICATIONS

Chen et al (Int J Radiation Oncol Biol Phys, vol. 84, No. 5, pp. e621-e630, 2012) (Year: 2012).*
Sheng et al (Medicine (Baltimore). Jun. 2015;94(24):e941) (Year: 2015).*
Skolnick et al (Trends Biotechnol. Jan. 2000;18(1):34-9) (Year: 2000).*
Burgess et al. (J. Cell Biol. 111:2129-2138, 1990) (Year: 1990).*
Miosge (Proc Natl Acad Sci U S A. Sep. 15, 2015;112(37):E5189-98) (Year: 2015).*
Bork (Genome Research, 2000, 10:398-400) (Year: 2000).*
Warzocha et al (Leukemia and Lymphoma (1997) vol. 24. pp. 267-281) (Year: 1997).*
McKeague et al (J Nucleic Acids. 2012;2012:748913. Epub Oct. 24, 2012) (Year: 2012).*
Vajdos et al. (J Mol Biol. Jul. 5, 2002;320(2):415-28 (Year: 2002).*
Brown et al. (J Immunol. May 1996; 156(9):3285-91 (Year: 1996).*
Guido et al (Curr Med Chem. 2008;15(1):37-46) (Year: 2008).*
Clark et al (J. Med. Chem., 2014, 57 (12), pp. 5023-5038) (Year: 2014).*
Waiker et al (J Am Soc Nephrol. Jan. 2012; 23(1): 13-21) (Year: 2012).*

(Continued)

*Primary Examiner* — Brian Gangle
*Assistant Examiner* — Andrea K McCollum
(74) *Attorney, Agent, or Firm* — The Roy Gross Law Firm, LLC; Roy Gross

(57) ABSTRACT

A method is provided for treating a cancer patient non-responsive to treatment with a cancer therapy by treating the patient with said cancer therapy in combination with an agent that blocks the activity of a dominant factor selected among the plurality of host-driven resistance factors generated in response to treatment of the cancer patient with the cancer therapy, these factors having a fold-change predictive of a non-favorable response of the cancer patient to the treatment with the cancer therapy.

14 Claims, 2 Drawing Sheets

(56) References Cited

OTHER PUBLICATIONS

Brooks (Genome Res. 2012. 22: 183-187) (Year: 2012).*
Mckean et al (Am Soc Clin Oncol Educ Book. May 2020;40:e275-e291) (Year: 2020).*
Aberuyi et al (Front Oncol. 2019; 9: 1496) (Year: 2019).*
Sporn et al, "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042 (Year: 1997).*
HogenEsch et al (J Control Release. Dec. 1, 20120; 164(2): 183-186.) (Year: 2012).*
Wang et al (JCI Insight. Dec. 6, 2018; 3(23): e122360) (Year: 2018).*
Cohen (J Mol Med (Berl). Mar. 2013;91(3):357-68. Epub Sep. 28, 2012) (Year: 2013).*
Turano et al (Membranes (2021), 11, 312) (Year: 2021).*
Chen et al (Drug Design, Development and Therapy 2015:9 3455-3458) (Year: 2015).*
Lin et al ( Anticancer Research Mar. 2017, 37 (3) 963-967) (Year: 2017).*
InVivoMab anti-mouse IL-7R product sheet (cat. #BE002), downloaded from https://bioxcell.com/invivomab-anti-mouse-il-7ra-cd127 on Aug. 26, 23). (Year: 2023).*
Wei et al (Biol Res 53, 20 (2020) (Year: 2020).*
Alishekevitz et al., Macrophage-Induced Lymphangiogenesis and Metastasis following Paclitaxel Chemotherapy Is Regulated by VEGFR3. Cell Reports, 17(5), 1344-1356, 2016.
Beyar-Katz et al., Bortezomib-induced pro-inflammatory macrophages as a potential factor limiting anti-tumour efficacy. The Journal of Pathology, 239(3), 262-273, 2016.
Chen et al., Intermittent Metronomic Drug Schedule Is Essential for Activating Antitumor Innate Immunity and Tumor Kenograft Regression. Neoplasia, 16(1), 84-W27, 2014.
De Henau et al., Overcoming resistance to checkpoint blockade therapy by targeting PI3Ky in myeloid cells. Nature, 539(7629), 443-447, 2016.
De Palma et al., Macrophage Regulation of Tumor Responses to Anticancer Therapies. Cancer Cell, 23(3), 277-286, 2013.
Doloff et al. VEGF Receptor Inhibitors Block the Ability of Metronomically Dosed Cyclophosphamide to Activate Innate Immunity-Induced Tumor Regression. Cancer Research, 72(5), 1103-1115, 2012.
Duraiswamy et al., Dual Blockade of PD-1 and CTLA-4 Combined with Tumor Vaccine Effectively Restores T-Cell Rejection Function in Tumors. Cancer Research, 73(12), 3591-3603, 2013.
Gajewski et al., Innate and adaptive immune cells in the tumor microenvironment. Nature Immunology, 14(10), 1014-1022, 2013.
Giesen et al., Highly multiplexed imaging of tumor tissues with subcellular resolution by mass cytometry. Nature Methods, 11(4), 417-422, 2014.
Gingis-Velitski et al., Host Response to Short-term, Single-Agent Chemotherapy Induces Matrix Metalloproteinase-9 Expression and Accelerates Metastasis in Mice. Cancer Research, 71(22), 6986-6996, 2011.
Hughes et al., Matrigel: A complex protein mixture required for optimal growth of cell culture. Proteomics, 10(9), 1886-1890, 2010.
Katz et al., "Host effects contributing to cancer therapy resistance" Drug Resist Updat. 19:pp. 33-42. (2015).
Kim et al., Assaying Cell Cycle Status Using Flow Cytometry. Current Protocols in Molecular Biology, 111: 28 6 pp. 1-11. (2016).
Kim et al., "Macrophages and mesenchymal stromal cells support survival and proliferation of multiple myeloma cells", British Journal of Haematology; 158(3): pp. 336-346. (2012).
Kodumudi et al., "Immune Checkpoint Blockade to Improve Tumor Infiltrating Lymphocytes for Adoptive Cell Therapy" PloS one 11(4):e0153053. (2016).

Topalian et al., "Immune checkpoint blockade: a common denominator approach to cancer therapy", Cancer Cell 27 (4): pp. 450-461. (2015).
Ma et al., "Anticancer Chemotherapy-Induced Intratumoral Recruitment and Differentiation of Antigen-Presenting Cells", Immunity. 38(4): pp. 729-741 (2013).
Makkouk et al., "Cancer Immunotherapy and Breaking Immune Tolerance-New Approaches to an Old Challenge", Cancer Res. 75(1): pp. 5-10 (2015).
Ostrand-Rosenberg et al., "Myeloid-Derived Suppressor Cells: Linking Inflammation and Cancer", J. Immunol. 182(8):4499-4506, 2009.
Pardoll, "The blockade of immune checkpoints in cancer immunotherapy", Nat Rev Cancer. 12(4): 252-264, (2012).
Postow et al., "Immune Checkpoint Blockade in Cancer Therapy", Journal of Clinical Oncology vol. 33, No. 17, pp. 974-982 (2015).
Qiu et al., "Extracting a Cellular Hierarchy from High-dimensional Cytometry Data with SPADE", Nat Biotechnol. ; 29(10): 886-891, 2011.
Rachman-Tzemah et al., Blocking Surgically Induced Lysyl Oxidase Activity Reduces the Risk of Lung Metastases, Cell Reports; 19(4): pp. 774-784, (2017).
Ran et al., "Double nicking by RNA-guided CRISPR Cas9 for enhanced genome editing specificity", Cell. 12; 154(6): 1380-1389, 2013.
Ran et al., "Genome engineering using the CRISPR-Cas9 system", Nat Protoc. 8(11): 2281-2308, 2013.
Romano et al., The therapeutic promise of disrupting the PD-1/PD-L1 immune checkpoint in cancer: unleashing the CD8 T cell mediated anti-tumor activity results in significant, unprecedented clinical efficacy in various solid tumors, Journal for Immuno Therapy of Cancer 3:15, 2015.
Sato et al., "Interleukin 10 in the tumor microenvironment: a target for anticancer immunotherapy", Immunol Res. 51:170-182, 2011.
Shaked, "Balancing efficacy of and host immune responses to cancer therapy: the yin and yang effects" Nat Rev Clin Oncol (2016).
Shaked et al., "Antiangiogenic Strategies on Defense: On the Possibility of Blocking Rebounds by the Tumor Vasculature after Chemotherapy", Cancer Res. 67(15): pp. 7055-7058 (2007).
Shaked et al., "Therapy-Induced Acute Recruitment of Circulating Endothelial Progenitor Cells to Tumors", Science. 313(5794): 1 pp. 785-787. (2006).
Shaked et al., "Rapid Chemotherapy-Induced Acute Endothelial Progenitor Cell Mobilization: Implications for Antiangiogenic Drugs as Chemosensitizing Agents", Cancer Cell. 14(3): pp. 263-273 (2008).
Sharma, P., Hu-Lieskovan, S., Wargo, J. A., & Ribas, A. (2017). Primary, Adaptive, and Acquired Resistance to Cancer Immunotherapy. Cell, 168(4), 707-723, 2017.
Swart et al., "Combination Approaches with immune-Checkpoint Blockade in Cancer Therapy" Frontiers in Oncology. 6:233 (2016).
Sun et al., "IL-10 and PD-1 cooperate to limit the activity of tumor-specific CD8 + T cells" Cancer Res. 75(8): 1635-1644, 2015.
Timaner et al., "Analysis of the Stromal Cellular Components of the Solid Tumor Microenvironment Using Flow Cytometry" Curr Protoc Cell Biol. 70:19 pp. 81-82 (2016).
Kruisbeek, A. M. (1992). In Vivo Depletion of CD4- and CD8-Specific T Cells. Current Protocols in Immunology, 1(1), 4.1.1-4.1.5, 2001.
Winter, Stuart S. et al. (2013) ATP Binding Cassette C1 (ABCC1/MRP1)-mediated drug efflux contributes to disease progression in T-lineage acute lymphoblastic leukemia, Health (Irvine Calf) 5(5A): 41-50. doi:10.4236/health.2013.55A005.
Wei, Jin et al. (2017) "MUC1 induces acquired chemoresistance by upregulating ABCB1 in EGFR-dependent manner", Cell Death and Disease 8, e2980, 13 pages. doi: 10.1038/cddis.2017.378.
Pierard, Laure et al. (2017) "Involvement of Angiogenin in Sunitinib Resistance in Human Renal Cell Carcinoma", The Journal of Urology vol. 197, No. 4S, Supplement. https://doi.org/10.1016/j.iuro.2017.02.3352.
Goncalves, Kevin A., et al. (2016). "Angiogenin Promotes Hematopoietic Regeneration by Dichotomously Regulating Quies-

(56) References Cited

OTHER PUBLICATIONS cence of Stem and Progenitor Cells", Cell Press 166, 894-906. http://dx.doi.org/10.1016/j.cell.2016.06.042.

Efferth, Thomas, et al. (2006). "Expression profiling of ATP-binding cassette transporters in childhood T-cell acute lymphoblastic leukemia", Molecular Cancer Therapeutics 2006;5(8). DOI: 10.1158/1535-7163.MCT-06-0086.

Yamazaki et al. (2017). "Cytokine biomarkers to predict antitumor responses to nivolumab suggested in a phase 2 study for advanced melanoma". Cancer science, 108.5: pp. 1022-1031.(2017). DOI: 10.1111/cas.13226.

Tian et al., "A novel cancer vaccine with the ability to simultaneously produce anti-PD-1 antibody and GM-CSF in cancer cells and enhance Th1-biased antitumor immunity" Signal Transduction and Targeted Therapy (2016) 1, 16025, 10 pages. doi: 10.1038/sigtrans.2016.25.

Dronca et al., "Bim and soluble PD-L1 (sPD-L1) as predictive biomarkers of response to anti-PD-1 therapy in patients with melanoma and lung carcinoma" Journal of Clinical Oncology, 2017, 35 No. 15 suppl, Abstract 11534. DOI: 10.1200/JCO.2017.35.15_suppl.11534.

Sanmamed et al., "Serum Interleukin-8 Reflects Tumor Burden and Treatment Response across Malignancies of Multiple Tissue Origins" Clinical Cancer Research, 2014, 20(22): 5697-5707. doi: 10.1158/1078-0432.CCR-13-3203.

Sznol et al., "Survival and long-term follow-up of safety and response in patients (pts) with advanced melanoma (MEL) In a phase I trial of nivolumab (anti-PD-1; BMS-936558; ONO-4538)" Journal of Clinical Oncology, 2013, 31 No. 18 suppl, Abstract CRA9006/\. DOI: 10.1200/jco.2013.31.18_suppl.cra9006 Journal of Clinical Oncology 31, No. 18_suppl.

Tockman et al., "Considerations in Bringing a Cancer Biomarker to Clinical Application" Cancer Research, 1992, 52:2711s-2718s. PMID: 1563002.

Choudhary et al. "Interleukin-6 role in head and neck squamous cell carcinoma progression" World Journal of Otorhinolaryngology-Head and Neck Surgery, 2016, 2, pp. 90-97. http://dx.doi.org/10.1016/j.wjorl.2016.05.002.

Krishnamurthy et al. "Endothelial Interleukin-6 defines the tumorigenic potential of primary human cancer stem cells" Stem Cells, 2014, 32(11): 2845-2857. doi:10.1002/stem.1793.

Merhi et al. "Squamous Cell Carcinomas of the Head and Neck Cancer Response to Programmed Cell Death Protein-1 Targeting and Differential Expression of Immunological Markers: A Case Report", Frontiers in Immunology, 2018, vol. 9, Article 1769, pp. 1-10. doi: 10.3389/fimmu.2018.01769.

Lee et al. "Current concepts in the diagnosis and management of cytokine release syndrome," 2014, Blood, vol. 124, No. 2, pp. 188-195. DOI 10.1182/blood-2014-05-552729.

Rotz et al. "Severe cytokine release syndrome in a patient receiving PD-1-directed therapy" Pediatric Blood & Cancer, 2017, 64: e26642, 5 pages. DOI: 10.1002/pbc.26642.

Anonymous: "FAM83 Proteins Promote Tumorigenesis and Drug Resistance", Cancer Discovery, 2012, vol. 2, No. 10, 1 page. DOI: 10.1158/2159-8290.CD-RW2012-133.

Chen et al., Analysis of Immune Signatures in Longitudinal Tumor Samples Yields Insight into Biomarkers of Response and Mechanisms of Resistance to Immune Checkpoint Blockade. Cancer Discovery, 6(8), 827-837, 2016. doi: 10.1158/2159-8290.CD-15-1545.

Hamid et al., "A prospective phase II trial exploring the association between tumor microenvironment biomarkers and clinical activity of ipilimumab in advanced melanoma". Journal of translational medicine, 9.1:204 (2011). doi: 10.1186/1479-5876-9-204.

Juric et al., "MMP-9 inhibition promotes anti-tumor immunity through disruption of biochemical and physical barriers to T-cell trafficking to tumors", PLOS ONE 13(11), 2018. https://doi.org/10.1371/journal.pone.0207255.

Munoz et al., "Highly Efficacious Nontoxic Preclinical Treatment for Advanced Metastatic Breast Cancer Using Combination Oral UFTCyclophosphamide Metronomic Chemotherapy, Cancer Res 2006; 66: (7), 3386-3391, 2006. doi:10.1158/0008-5472.CAN-05-4411.

Kruger et al., Antimetastatic Activity of a Novel Mechanism-Based Gelatinase Inhibitor; Cancer Res 2005; 65: (9), 3523-3526, 2005. DOI: 10.1158/0008-5472.CAN-04-3570.

Fujiu et al., "A heart-brain-kidney network controls adaptation to cardiac stress through tissue macrophage activation" Nature Medicine, vol. 23, No. 5, 611-622, 2017. doi:10.1038/nm.4326.

Bonfil et al., "Inhibition of human prostate cancer growth, osteolysis and angiogenesis in a bone metastasis model by a novel mechanism-based selective gelatinase inhibitor", Int. J. Cancer: 118, 2721-2726 (2006). DOI 10.1002/ijc.21645.

Bent, et al., "A senescence secretory switch mediated by PI3K/AKT/mTOR activation controls chemoprotective endothelial secretory responses" Genes & Development 30:1-11, 2016. doi: 10.1101/gad.284851.116. Epub Aug. 26, 2016. PMID: 27566778; PMCID: PMC5024680.

Karachaliou et al., "Interferon-gamma (INFG), an important marker of response to immune checkpoint blockade (ICB) in non-small cell lung cancer (NSCLC) and melanoma patients." Journal of Clinical Oncology, 2017, 35(15 suppl) Abstract 11504. DOI: 10.1200/JCO.2017.35.15_suppl.11504.

Kindler et al., "Biomarkers of pembrolizumab (P) activity in mesothelioma (MM): Results from a phase II trial." Oncology, 2017, 35 (15 suppl) Abstract 8557. DOI: 10.1200/JCO.2017.35.15_suppl.8557.

Chunlan, H. "Current status of treatment of multiple myeloma". Journal of Military Surgeon in Southwest China, vol. 13, No. 4, 704-707, Jul. 15, 2011.

Hirotake Tsukamoto et al., "Combined Blockade of IL6 and PD-1/PD-L1 Signaling Abrogates Mutual Regulation of Their Immunosuppressive Effects in the Tumor Microenvironment" American Association for Cancer Research, Cancer Research, 78(17), 5011-5022, Sep. 1, 2018. doi: 10.1158/0008-5472.CAN-18-0118. Epub Jul. 2, 2018. PMID: 29967259.

Xiao-Yun Li et al., "Doxorubicin resistance induces IL6 activation in the colon cancer cell line LS180" Oncology Letters, 16: 5923-5929, 2018. doi: 10.3892/ol.2018.9360. Epub Aug. 2, 20183. PMID: 30344742; Pmcid: PMC6176352.

* cited by examiner

METHOD OF TREATING CANCER WITH A CANCER THERAPY IN COMBINATION WITH ANOTHER THERAPEUTIC AGENT

CROSS-REFERENCE TO RELATED APPLICATIONS

This application claims the benefit of priority of non-provisional U.S. application Ser. No. 16/218,177, filed on Dec. 12, 2018. The disclosure of the prior application is considered part of and is incorporated by reference in its entirety in the disclosure of this application.

FIELD OF THE INVENTION

The present invention is in the field of oncology and particularly relates to a method of treatment of a cancer patient with a cancer therapy in combination with another therapeutic agent.

BACKGROUND

One of the major obstacles in clinical oncology is that tumors often develop resistance to therapy even when an initial tumor response to treatment is observed. Many studies have focused on the contribution of mutations and genetic aberrations in the tumor cells which promote drug resistance and can explain tumor re-growth. However, studies have demonstrated that the host, in response to cancer therapy, generates pro-tumorigenic and pro-metastatic effects which in turn contribute to tumor re-growth, and therefore negate the anti-tumor activity of the drug (for reviews see Katz and Shaked, 2015; Shaked, 2016).

Host-mediated responses to anti-cancer treatment modalities may be molecular and/or cellular responses. Upon treatment with chemotherapeutic drugs, host bone marrow derived cells (BMDCs) are mobilized from the bone marrow compartment, colonize the treated tumor and contribute to tumor angiogenesis and cancer re-growth, thereby promoting therapy resistance (Shaked et al., 2006, 2008). Cancer therapy also induces pro-tumorigenic activation of various immune cells such as macrophages and antigen presenting cells (Beyar-Katz et al., 2016; De Palma and Lewis, 2013; Kim et al. 2012; Ma et al., 2013). Overall, these aforementioned studies indicate that host-mediated molecular and cellular responses to different anti-cancer treatments involve the activation or education of immune cells as well as the secretion of various pro-tumorigenic factors. These combined effects contribute to tumor re-growth and resistance to therapy. This relatively new phenomenon has made a paradigm shift in understanding cancer progression and resistance to therapy.

Recently, a new treatment modality, an immunotherapy using immune checkpoint inhibitors (ICIs), is revolutionizing cancer therapy. Such immune-modulating drugs have shown remarkable successes for the treatment of advanced malignancies (including stage IV) such as melanoma, prostate, non-small cell lung cancer, renal cell carcinoma and also some hematological malignancies (Postow et al., 2015). Although the human immune system is capable of recognizing and mounting a response to cancerous cells, this response is often circumvented by tumor-derived inhibition resulting in immune tolerance. In this regard, tumor-infiltrating lymphocytes (TILs), such as tumor antigen-specific $CD8^+$ cytotoxic T lymphocytes (CTLs) and natural killer (NK) cells, have been found to colonize the tumor microenvironment (Gajewski et al., 2013). Yet, at the tumor site, they completely lack the ability to act against tumor cells (Ostrand-Rosenberg and Sinha, 2009). This is due to direct inhibitory effects of factors secreted by cancer cells, stromal cells or other suppressive immune cells such as myeloid derived suppressor cells (MDSCs) and T regulatory cells (Tregs) (Makkouk and Weiner, 2015). For instance, IL-10 is frequently upregulated in various types of cancer, and was shown to suppress the immune system (Sato et al., 2011). Thus, identifying molecules that negatively regulate the immune system against tumor cells, will lead to the development of immunomodulatory drugs that support the activation of immune cells against tumors.

Of specific interest are immune checkpoint proteins, such as CTLA-4, PD-1 and its ligand, PD-L1. These checkpoint proteins are expressed by tumor cells or other immune cells and contribute to the exhaustion of CTLs (Postow et al., 2015; Topalian et al., 2015). Specifically, they keep immune responses in check, and inhibit T cell killing effects against tumor cells. As such, checkpoint inhibitors have been developed in order to inhibit the immune suppression effects. Currently, antibodies blocking the immune checkpoints, CTLA-4 and PD-1 or its ligand PD-L1 have been developed (Pardoll, 2012). These ICIs are currently in use in the clinic for the treatment of various malignancies with some promising and remarkable successes (Romano and Romero, 2015). However, ICIs have shown therapeutic benefit only for a limited portion of cancer patients (~10-20%). For example, pooled data from clinical studies of ipilimumab, a CTLA-4 blocking antibody, revealed that the duration of clinical response is around 3 years, and can last up to 10 years. However, this dramatic therapeutic effect is only observed in a subset of patients (~20%). Thus, the majority of patients exhibit intrinsic resistance mechanisms to such therapies. Yet, the molecular aspects that define the sub-population of patients that are responsive to ICIs are not fully clear. It has been suggested that markers, such as PD-L1 expression by tumor cells, mutational burden, and lymphocytic infiltrates could predict the cancer patients that will respond to immunotherapy. However, these aforementioned biomarkers do not always correlate with tumor responsiveness to immunotherapy or resistance of patients to ICIs. Therefore, additional possible mechanisms are still unknown.

In the Applicant's International Patent Application No. PCT/IL2018/050608 filed on Jun. 4, 2018, published as WO 2018/225062, the entire contents of which are hereby incorporated herein by reference, a method of predicting personalized response to cancer treatment with a cancer therapy was described by identification of a plurality of factors/biomarkers induced by the cancer patient into the circulation in response to said cancer therapy ("host response") and determining how a change in the levels of each of one or more of the plurality of factors as compared to a reference level, predicts a favorable or a non-favorable response of the cancer patient to the treatment with said cancer therapy.

It would be highly desirable to unveil host-mediated cellular and molecular mechanisms that contribute to tumor resistance to all modalities of cancer therapy including the promising ICI therapy modality. This will permit development of strategies to block such unwanted host effects and will improve therapeutic outcome and delay resistance to cancer therapy.

SUMMARY OF THE INVENTION

The present invention is based on previous studies mentioned hereinbefore in the Background section of the application that show that a cancer patient (the "host"), in response to a cancer therapy, may generate and induce into the host circulation a set of host-driven resistance factors to said cancer therapy, that may limit or counteract the effectiveness of the patient treatment with the cancer therapy modality/drugs applied to said patient. The determination of these factors allows the prediction in a personalized form of the favorable or non-favorable response of the patient to the treatment with the cancer therapy modality/drugs. These factors, herein designated interchangeably "factors" or "biomarkers", are factors, mainly cytokines, chemokines, growth factors, soluble receptors, enzymes and other molecules produced by the host cells, either at different organs or at the tumor microenvironment, in response to the cancer therapy with which the patient is treated.

Thus, in one aspect, the present invention relates to a method of treating a cancer patient with a cancer therapy, the method comprising the steps of:
  (i) performing an assay on a blood sample selected from blood plasma, whole blood, blood serum or peripheral blood mononuclear cells obtained from the cancer patient at a time point after a session of treatment with said cancer therapy, to determine the levels of one or more of a plurality of host-driven resistance factors that are driven by the host ("the cancer patient") in response to treatment with said cancer therapy, said one or more of the plurality of factors promoting in a personalized form responsiveness or non-responsiveness of the cancer patient to the treatment with said cancer therapy;
  (ii) obtaining reference levels for each of the one or more of the plurality of the host-driven resistance factors of step (i) by determining the levels of each of said factors in a blood sample of the same type of the blood sample of step (i), obtained from the cancer patient at a time point before said session of treatment with the cancer therapy;
  (iii) establishing the fold change for each of the one or more of the plurality of the host-driven resistance factors of step (i) by comparing the level of each host-driven resistance factor of step (i) with the reference level of step (ii) for the same factor;
  (iv) determining that the cancer patient has a favorable or a non-favorable response to the treatment with said cancer therapy based on the fold change established in step (iii) for one or more of the plurality of host-driven resistance factors of step (i); and
  (iva) if the cancer patient has a non-favorable response to the treatment with said cancer therapy based on the fold change established in step (iii) for one or more of the plurality of the host-driven resistance factors, then selecting a dominant factor among the one or more host-driven resistance factors showing a fold change indicative of said non-favorable response, and treating the patient with a therapeutically effective amount of an agent that blocks the activity of the selected dominant host-driven resistance factor, or the receptor thereof, in combination with a therapeutically effective amount of the cancer therapy drug or with therapeutic doses of radiation when the cancer therapy is radiation therapy; or
  (ivb) if the cancer patient has a favorable response to the treatment with said cancer therapy based on the fold change established in step (iii) for one or more of the plurality of host-driven resistance factors, then continuing the treatment of the cancer patient with the same cancer therapy.

In a certain embodiment, the invention relates to a method for treatment of a cancer patient non-responsive to treatment with a cancer therapy, the method comprising administering to the cancer patient a therapeutically effective amount of an agent that blocks the activity of a dominant factor, or the receptor thereof, in combination with a therapeutically effective amount of a drug used in the cancer therapy or with therapeutic doses of radiation when the cancer therapy is radiation therapy, the dominant factor being selected among the plurality of host-driven resistance factors generated in response to treatment of the cancer patient with the cancer therapy, the plurality of host-driven factors having a fold-change predictive of a non-favorable response of the cancer patient to the treatment with the cancer therapy, wherein the fold change is established by comparing: (i) the level of the host-driven resistance factors in a blood sample selected from blood plasma, whole blood, blood serum or peripheral blood mononuclear cells, obtained from the cancer patient after a session of treatment with the cancer therapy, with (ii) a reference level obtained from a blood sample of the same type of (i), obtained from the cancer patient before said session of treatment with the cancer therapy.

In another aspect, the present invention relates to a cancer drug, for use in the treatment of cancer in a patient non-responsive to said drug, comprising administering a therapeutically effective amount of the drug in combination with a therapeutically effective amount of an agent that blocks the activity of a dominant factor, or the receptor thereof, the dominant factor being selected among the plurality of host-driven resistance factors generated in response to treatment of the cancer patient with the cancer drug, the plurality of host-driven resistance factors having a fold-change predictive of a non-favorable response of the cancer patient to the treatment with the cancer drug, wherein the fold change is established by comparing: (i) the level of the host-driven resistance factors in a blood sample selected from blood plasma, whole blood, blood serum or peripheral blood mononuclear cells, obtained from the cancer patient after a session of treatment with the cancer drug, with (ii) a reference level obtained from a blood sample of the same type of (i), obtained from the cancer patient before said session of treatment with the cancer drug.

In another aspect, the present invention relates to an agent that blocks the activity of a dominant factor, or of the receptor thereof, for use in radiotherapy treatment of cancer in a patient non-responsive to radiotherapy, comprising administering a therapeutically effective amount of the agent in combination with therapeutic doses of radiation, the dominant factor being selected among the plurality of host-driven resistance factors generated in response to treatment of the cancer patient with radiotherapy, the plurality of host-driven resistance factors having a fold-change predictive of a non-favorable response of the cancer patient to the treatment with the radiotherapy, wherein the fold change is established by comparing: (i) the level of the host-driven resistance factors in a blood sample selected from blood plasma, whole blood, blood serum or peripheral blood mononuclear cells, obtained from the cancer patient after a session of treatment with the radiotherapy, with (ii) a reference level obtained from a blood sample of the same type of (i), obtained from the cancer patient before said session of treatment with the radiotherapy.

BRIEF DESCRIPTION OF THE FIGURES

FIG. 1A shows that treatment with 240 µg doxorubicin (DOX) caused an increased plasma level of IL-6 in BALB/c mice. FIG. 1B shows that treatment with doxorubicin in combination with anti-IL-6 (squares) resulted in improved anti-tumor effect compared to control (circles), with doxorubicin (diamonds), or anti-IL-6 (triangles).

DETAILED DESCRIPTION

Figure 1A:
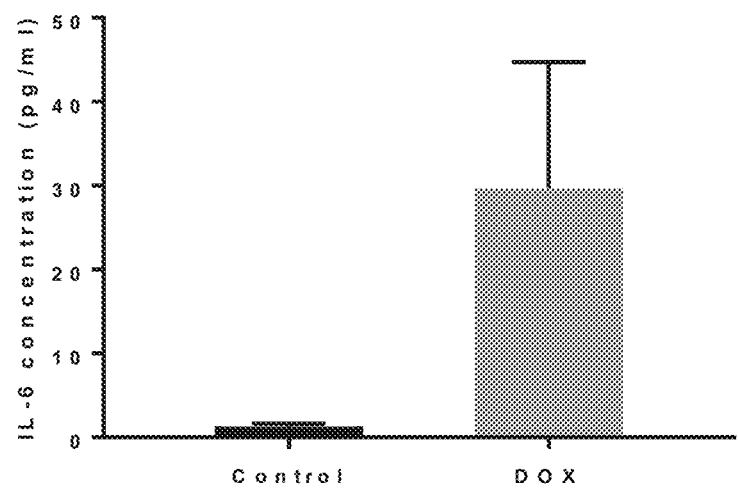
FIGS. 1A-1B show host-induction of IL-6 in response to chemotherapeutic treatment and the effect of blocking IL-6 in the treatment with the chemotherapeutic agent.

Before describing the methods of the invention, it should be understood that this invention is not limited to the particular methodology and protocols as described herein. It is also to be understood that the terminology used herein is for the purpose of describing particular embodiments of the invention only and, if not defined otherwise, it is not intended to limit the scope of the present invention which will be recited in the appended claims.

It must also be noted that as used herein and in the appended claims, the singular forms "a", "an", and "the" include plural reference unless the context clearly dictates otherwise.

As used herein, the term "a cancer therapy" may be used interchangeably with the term "a cancer-modality therapy", and include plural reference, namely, one single modality therapy or a combination of two or more modality therapies.

As used herein, the terms "induced", "driven" and "generated" are used interchangeably to denote the factors induced into the circulation by the cancer patient in response to the cancer therapy ("host-response").

As used herein, the terms "a drug" and "the drug" refer to a single drug, a combination of drugs of the same modality such as two or more chemotherapeutic drugs, or a combination of drugs related to different cancer therapy modalities.

In accordance with the invention, the cancer therapy is related to treatment of all types of cancer, primary or metastatic, selected from sarcomas, carcinomas, myelomas, lymphomas and leukemias. In certain embodiments, the cancer is of the sarcoma type, e.g. soft tissue sarcoma, osteosarcoma. In certain embodiments, the cancer is a primary or a metastatic cancer including bladder, bone, breast, brain, cervical, colon, colorectal, esophageal, gastric cancer, gastrointestinal, glioblastoma, head and neck, head and neck squamous cell cancer, hepatocellular cancer, kidney, liver, lung including small cell lung cancer and non-small cell lung cancer (NSCLC), melanoma, nasopharyngeal, ovarian, pancreas, penile, prostate, skin, testicular, thymus, thyroid, urogenital, or uterine cancer, leukemia, lymphoma, multiple myeloma and sarcoma.

In certain embodiments, the cancer is a lymphoma, a cancer of the lymphatic system that may be a Hodgkin lymphoma or a non-Hodgkin lymphoma, either B-cell lymphoma or T-cell lymphoma.

In certain embodiments, the cancer is leukemia, that may be acute lymphocytic leukemia (ALL), acute myeloid leukemia (AML), chronic lymphocytic leukemia (CLL) or chronic myeloid leukemia (CML) In certain embodiments, the cancer is multiple myeloma.

As used herein, the terms "a cancer therapy", "a cancer-modality therapy' or "a cancer treatment modality" refer to any modality of cancer therapy or cancer treatment including, but without being limited to, chemotherapy, radiation therapy, surgery, targeted therapy (including all types of immunotherapy), anti-angiogenic therapy, hormonal therapy, photodynamic therapy, thermotherapy, and combinations thereof.

In certain embodiments, the cancer therapy is an adjuvant therapy, namely, an additional cancer treatment given after the main/primary treatment, which is usually surgery, to lower the risk of recurrence of the cancer. Examples of adjuvant therapy include chemotherapy, radiation therapy, hormone therapy, targeted therapy, In certain embodiments, the cancer therapy is a neoadjuvant therapy, namely, a cancer treatment given as a first step to shrink a tumor before the main/primary treatment, which is usually surgery, is given. Examples of neoadjuvant therapy include chemotherapy, radiation therapy, and hormone therapy.

In certain embodiments, the cancer-modality therapy is chemotherapy with chemotherapeutic drugs that target and kill cells that quickly grow and divide, as cancer cells do, but can also affect some fast-growing healthy cells. In certain embodiments, chemotherapy is used as the single treatment. In certain other embodiments, chemotherapy is used in combination with another cancer therapy such as surgery, radiation therapy or targeted therapy.

In certain embodiments, the chemotherapy is mono-chemotherapy with a sole chemotherapeutic drug. In other embodiments, the chemotherapy is carried out with a combination of two, three, four or more chemotherapeutic drugs. The chemotherapeutic drugs in both cases may be chosen from: (i) anthracyclines including doxorubicin, pegylated liposomal doxorubicin, and epirubicin; (ii) taxanes including paclitaxel, albumin-bound paclitaxel and docetaxel; (iii) 5-fluorouracil; (iv) cyclophosphamide; (v) platinum agents including cisplatin, oxaliplatin and carboplatin; (vi) vinorelbine; (vii) capecitabine; (viii) gemcitabine; (ix) ixabepilone; and (x) eribulin, particularly the combinations including doxorubicin (Adriamycin) and cyclophosphamide (AC) or including folinic acid, 5-fluorouracil and oxaliplatin (FOLFOX); or a combination of chemotherapy with another cancer therapy including surgery, radiation, or targeted cancer therapy.

Herein in the application, the brand name of a drug may be presented within brackets with an initial capital letter. For example, (Taxol™) is a brand name for paclitaxel (could be presented also as TAXOL or TAXOL®), (Adriamycin™) for doxorubicin, (Ellence™) for epirubicin, and (Taxotere™) for docetaxel.

In certain embodiments, treatment of breast cancer is carried out with paclitaxel. In certain other embodiments, treatment of breast cancer is carried out with the combination paclitaxel/carboplatin or with the combination Adriamycin/Cyclophosphamide (AC).

In certain embodiments, for treatment of advanced breast cancer that has spread, adjuvant chemotherapy is carried out with one single chemotherapeutic drug or a combination of 2 or 3 drugs chosen from: (i) anthracyclines such as doxorubicin, pegylated liposomal doxorubicin, and epirubicin: (ii) taxanes such as paclitaxel, docetaxel and albumin-bound paclitaxel; (iii) platinum agents such as cisplatin (Platinol™), oxaliplatin and carboplatin; (iv) vinorelbine (Navelbine™); (v) capecitabine (Xeloda™); (vi) gemcitabine (Gemzar™); (vii) ixabepilone; and (viii) eribulin (Halaven™).

In certain embodiments, for treatment of bowel, colon or colorectal cancer, adjuvant chemotherapy is carried out with one or more drugs chosen from 5-fluorouracil (5-FU), leucovorin, capecitabine, irinotecan (Camptosar™), oxaliplatin (Eloxatin™) or a combination of trifluridine and tipiracil (Lonsurf™) depending on the stage of the cancer. In certain embodiments, a combination of 2 to 4 of chemo drugs is chosen such as FOLFOX™ (5-FU-leucovorin-oxaliplatin), FOLFIRI™ (5-FU+leucovorin+irinotecan), FOLFOX-IRLI™ (5-FU+leucovorin+oxaliplatin+irinotecan), or CAPEOX™ (capecitabine+oxaliplatin) or capecitabine alone may be used.

In certain embodiments, treatment of testicular cancer is carried out with a combination of the chemotherapy drugs cisplatin, etoposide and ifosfamide (PEI).

In certain embodiments, the cancer-modality therapy is radiation therapy (herein also sometimes identified as "radiotherapy") with high-energy radiation, e.g., x-rays, gamma rays, electron beams, or protons, to shrink tumors and destroy or damage cancer cells thus preventing them from growing and dividing. Treatment of a cancer patient with radiation therapy is carried out with multiple doses of radiation (not with drugs) and host-derived circulating factors are generated by the cancer patient after the application of each dose of treatment, from which a dominant factor is selected for its blockade in order to continue the treatment with the radiotherapy. Thus, when radiation is the cancer modality used in the invention, the treatment of the cancer patient non-responsive to radiation therapy is carried out with a therapeutically effective amount of an agent that blocks the activity of the dominant factor, or of the receptor thereof, in combination with therapeutic doses of radiation.

In certain embodiments, the cancer therapy modality is surgery for removal of localized cancerous solid tumors, and optionally surrounding tissue, during an operation. Surgery may be the curative treatment or the primary treatment in combination with chemotherapy or radiation therapy prior to, or after, surgery. Host-derived circulating factors are generated by the cancer patient after the surgery and neutralization of upregulated pro-tumorigenic or pro-metastatic induced factors is necessary to avoid recurrence or spread of the tumors, independently if the surgery is followed by chemotherapy or radiation therapy or not.

In certain embodiments, the cancer therapy is targeted cancer therapy, sometimes called "molecularly targeted drugs" or "molecularly targeted therapies". These therapies use drugs or other substances to identify and attack specific types of cancer cells with less harm to normal cells. Some targeted therapies block the growth and spread of cancer by interfering with specific molecules ("molecular targets"), e.g., enzymes or proteins found in cancer cells or in cells related to cancer growth, like blood vessels. In this way, the therapy targets molecules involved in the growth, progression, and spread of cancer cells, rather than simply interfering with all rapidly dividing cells as in traditional chemotherapy. Some targeted therapies are often cytostatic, namely, they block tumor cell proliferation, while standard chemotherapy agents are cytotoxic, and namely kill tumor cells. Other types of targeted therapies help the immune system kill cancer cells or deliver toxic substances directly to the cancer cells and kill them.

A good target is a target that plays a key role in cancer cell growth and survival. For example, proteins present in cancer cells but not in normal cells, or proteins more abundant in cancer cells, are potential good targets, particularly if they are known to be involved in cell growth or survival. An example is the human epidermal growth factor receptor 2 protein (HER-2) that is expressed at high levels on the surface of some cancer cells in breast and stomach tumors. Another example is cell growth signaling protein BRAF present in an altered form (BRAF V600E) in many melanomas. A further example is the creation of a fusion gene by chromosome abnormalities whose protein may drive cancer development, such as the BCR-ABL fusion protein present in some leukemia cells.

The main types of targeted therapy are small-molecule drugs and monoclonal antibodies.

In certain embodiments, the cancer therapy is targeted therapy with small-molecule drugs that enter cells easily and reach targets that are inside the cells.

In certain embodiments, the small molecules are proteasome inhibitors that block the action of proteasomes, cellular complexes that break down proteins. In certain embodiments, the proteasome inhibitors include, but not limited to, bortezomib (Velcade™), carfilzomib (Kyprolis™) and Ixazomib (Ninlaro™), all approved for treatment of multiple myeloma.

In certain embodiments, the small molecules are receptor tyrosine-kinase inhibitors (TKI) that inhibit the phosphorylation of the tyrosine kinases enzymes responsible for the activation of many proteins by signal transduction cascades. In certain embodiments, the TKIs include, but are not limited to: dasatinib (Sprycel™) that targets BCR-ABL and other kinases and was approved for treatment of CML; erlotinib (Tarceva™) and gefitinib (Iressa™) that target EGFR and approved for non-small cell lung cancer; imatinib mesylate (Gleevec™) that targets the BCR-ABL fusion protein and was approved for treatment of CLL and gastrointestinal stromal tumor; lapatinib (Tykerb™); nilotinib (Tarsigna™), for treatment of CML; pazopanib (Votrient™), that blocks tumor growth and inhibits angiogenesis, for treatment of advanced renal cell carcinoma (RCC); sorafenib (Nexavar™) for treatment of RCC and hepatocellular carcinoma (HCC); and sunitinib (Sutent™) approved for metastatic RCC.

In certain embodiments, the small molecules are serine-threonine kinase (STK) inhibitors including, but not limited to, dabrafenib (Tafinlar™); everolimus (Afinitor™); temsirolimus (Torisel™); trametinib (Mekinist™); and vemurafenib (Zelboraf™) that targets the mutant BRAF V660E protein and is approved for treatment of melanoma.

In certain embodiments, the targeted cancer therapy is immunotherapy with monoclonal antibodies (mAbs) that trigger the body's immune system to fight and destroy cancer cells. In certain embodiments, the mAb is a non-conjugated monoclonal antibody that binds to a target antigen on the surface of cancer cells and activates the immune system to attack the cancer cells or to block protein that helps the cancer cells grow and is located within or on surface of tumors or in the tumor microenvironment. Examples of mAbs for cancer therapy include: alemtuzumab (Campath™), that binds CD52 antigen found on lymphocytes, and approved for CLL; bevacizumab (Avastin™), that binds VEGF and is indicated for treatment of glioblastoma, renal cell carcinoma, and metastatic breast, lung, and colon cancer; cetuximab (Erbitux™) that targets EGFR and is indicated for treatment of colon cancer, metastatic colorectal cancer and head and neck cancer; daratumumab (Darzalex™) that targets CD38 and is indicated for treatment of multiple myeloma also in combination with bortezomib, melphalan and prednisone (VMP) in early stages of the disease; olaratumab (Lartruvo™), an mAb that targets PDGFR-alpha, a protein on cancer cells, and can be used with doxorubicin to treat soft tissue sarcomas; panitumumab (Vectibix™) targets EGFR and is indicated for treatment of metastatic colorectal cancer alone or in combination with FOLFOX™ chemotherapy; and trastuzumab (Herceptin™)

that targets HER2 protein and is indicated for treatment of certain breast and stomach cancer.

In certain embodiments, the targeted cancer therapy is anti-angiogenic therapy. In certain embodiments, the anti-angiogenic drug is a monoclonal antibody that targets VEGF, including the above-mentioned Bevacizumab™ and Panitumumab™ or block VEGF attachment to its receptors and this stops the blood vessels from growing. In certain embodiments, the antiangiogenic drug is a tyrosine-kinase inhibitor such as the above-mentioned sunitinib that stops the VEGF receptors from sending growth signals into the blood vessel cells.

In certain embodiments, the targeted therapy involves conjugated mAbs, also referred to as tagged, labeled or loaded antibodies, in which the mAb is linked to a chemotherapy drug or to a radioactive particle that is delivered directly to the cancer cells while the mAb functions as the homing agent and binds onto the target antigen in the cell. In certain embodiments, the conjugated mAb is a radiolabeled antibody with small radioactive particles attached to it, e.g., $^{90}$Y-ibritumomab tiuxetan (Zevalin™) that targets the CD20 antigen found on B cells and is used to treat some types of non-Hodgkin lymphoma. In certain embodiments, the conjugated mAb is a chemolabeled antibody also called antibody-drug conjugate (ADC), e.g., ado-trastuzumab emtansine or T-DM1 (Kadcyla®) that targets HER2, attached to the DM1 chemo drug, and is used to treat some breast cancer patients whose cancer cells have too much HER2.

In certain embodiments, the targeted cancer therapy is hormonal therapy for slowing or stopping the growth of hormone-sensitive tumors, which require certain hormones to grow, for example, in prostate and breast cancers.

In certain embodiments, the targeted cancer therapy is photodynamic therapy (PDT), more particularly vascular-targeted photodynamic therapy (VTP), recently approved for padeliporfin/WST-11 (Tookad™) for treatment of localized prostate cancer The host-driven factors/biomarkers identified by the method of the invention, after administration of a cancer therapy to a cancer patient, are specific to: (i) the cancer patient; and (ii) to the cancer therapy modality. In each modality, the response is specific also to the specific drug or combination of drugs used. In a combination of modalities, the response is specific to the combination of modalities used. This is the "host response" that provides specific information about the reaction of the cancer patient to the treatment and allows the prediction in a personalized form to help diagnose, plan treatment, find out how well treatment is working, or make a prognosis.

If the cancer therapy modality is, for example, chemotherapy with one single drug, the factors generated by the host/patient are specific to this particular drug. If the chemotherapy is carried out with a combination of two or more chemotherapeutic drugs, the factors generated by the host/patient are specific to this combination of the two or more chemotherapeutic drugs.

In certain embodiments, the biomarkers are molecular factors that may be cytokines, chemokines, growth factors, enzymes or soluble receptors. Some of these factors induce cells that affect the tumor and contribute to tumor angiogenesis and cancer re-growth, thereby promoting resistance to the therapy used. Examples of such cells include bone-marrow derived cells (BMDCs) that are mobilized from the bone-marrow compartment by cytokines and growth factors such as G-CSF and SDF-1α, and subsequently colonize the treated tumors and promote cancer therapy resistance, particularly, but not exclusively, chemotherapy resistance. Other cells are immune cells such as macrophages and antigen-presenting cells, or stromal cells within the tumor microenvironment which play a pivotal role in tumor progression.

The host-mediated cellular and molecular mechanisms that contribute to tumor resistance to a cancer therapy are based on the biological functions of the factors and/or cells generated in the host by the particular cancer therapy. Each factor may exhibit one or more biological functions or activities.

In certain embodiments, the factors are pro-tumorigenic and contribute to tumor growth. In certain embodiments, the pro-tumorigenic factors are pro-angiogenic. In other embodiments, the pro-tumorigenic factors are pro-inflammatory/chemotactic. In yet other embodiments, the pro-tumorigenic factors are proliferative growth factors.

In certain embodiments, the pro-angiogenic factors include, without being limited to, ANG (angiogenin); angiopoietin-1; angiopoietin-2; bNGF (basic nerve growth factor); cathepsin S; Galectin-7; GCP-2 (granulocyte chemotactic protein, CXCL6); G-CSF (granulocyte-colony stimulating factor); GM-CSF (granulocyte-macrophage colony stimulating factor, also known as colony-stimulating factor 2, CSF2); PAI-1 (plasminogen activator inhibitor-1); PDGF (platelet-derived growth factor) selected from PDGF-AA, PDGF-BB, PDGF-AB; PlGF (or PLGF, placental growth factor); PlGF-2; SCF (stem-cell factor); SDF-1 (CXCL12, stromal cell-derived factor-1); Tie2 (or TIE-2, an endothelial receptor tyrosine kinase); VEGF (vascular endothelial growth factor) selected from VEGF-A, VEGF-C and VEGF-D; VEGF-R1; VEGF-R2; and VEGF-R3.

In certain embodiments, the pro-inflammatory and/or chemotactic factors include, without being limited to, 6Ckine (CCL21, Exodus-2); angiopoietin-1; angiopoietin-2; BLC (CXCL13, B lymphocyte chemoattractant or B cell-attracting chemokine 1 (BCA-1); BRAK (CXCL14); CD186 (CXCR6); ENA-78 (CXCL5, Epithelial cell derived neutrophil activating peptide 78); Eotaxin-1 (CCL11); Eotaxin-2 (CCL24); Eotaxin-3 (CCL26); EpCAM (Epithelial cell adhesion molecule); GDF-15 (growth differentiation factor 15, also known as macrophage inhibitory cytokine-1, MIC-1); GM-CSF; GRO (growth-regulated oncogene); HCC-4 (CCL16, human CC chemokine 4); I-309 (CCL1); IFN-γ; IL-1α; IL-1β; IL-1R4 (ST2); IL-2; IL-2R; IL-3; IL-3Rα; IL-5; IL-6; IL-6R; IL-7; IL-8; IL-8 RB (CXCR2, interleukin 8 receptor, beta); IL-11; IL-12; IL-12p40; IL-12p70; IL-13; IL-13 R1; IL-13R2; IL-15; IL-15Rα; IL-16; IL-17; IL-17C; IL-17E; IL-17F; IL-17R; IL-18; IL-18BPa; IL-18 Rα; IL-20; IL-23; IL-27; IL-28; IL-31; IL-33; IP-10 (CXCL10, interferon gamma-inducible protein 10); I-TAC (CXCL11, Interferon-inducible T-cell alpha chemoattractant); LIF (Leukemia inhibitory factor); LIX (CXCL5, lypopolysaccharide-induced CXC chemokine); LRP6 (low-density lipoprotein (LDL) receptor-related protein-6); MadCAM-1 (mucosal addressin cell adhesion molecule 1); MCP-1 (CCL2, monocyte chemotactic protein 1); MCP-2 (CCL8); MCP-3 (CCL7); MCP-4 (CCL13); M-CSF (macrophage colony-stimulating factor, also known as colony stimulating factor 1 (CSF1); MIF (macrophage migration inhibitory factor); MIG (XCL9, Monokine induced by gamma interferon); MIP-1 gamma (CCL9, macrophage inflammatory protein-1 gamma); MIP-1α (CCL3); MIP-1β; MIP-1δ (CCL15); MIP-3α (CCL20); MIP-30 (CCL19); MPIF-1 (CCL23, Myeloid progenitor inhibitory factor 1); PARC (CCL18, pulmonary and activation-regulated chemokine); PF4 (CXCL4, platelet factor 4); RANTES (CCL5, regulated on activation, normal T cell expressed and secreted); Resistin; SCF; SCYB16 (CXCL16, small inducible cytokine B16); TACI (transmembrane activator and CAML interactor); TARC (CCL17, CC thymus and activation related chemokine); TSLP (Thymic stromal lymphopoietin); TNF-α (tumor necrosis factor-α); TNF-R1; TRAIL-R4 (TNF-Related Apoptosis-Inducing Ligand Receptor 4); TREM-1 (Triggering Receptor Expressed On Myeloid Cells 1).

In certain embodiments, the proliferative factors include, without being limited to, Activin A; Amphiregulin; Axl (AXL, a receptor tyrosine kinase); BDNF (Brain-derived neurotrophic factor); BMP4 (bone morphogenetic protein 4); cathepsin S; EGF (epidermal growth factor); FGF-1 (fibroblast growth factor 1); FGF-2 (also known as bFGF, basic FGF); FGF-7; FGF-21; Follistatin (FST); Galectin-7; Gas6 (growth arrest-specific gene 6); GDF-15; HB-EGF (heparin-binding EGF); HGF; IGFBP-1 (Insulin-like growth factor binding protein-1); IGFBP-3; LAP (Latency-associated peptide); NGF-R (nerve growth factor receptor); NrCAM (neuronal cell adhesion molecule); NT-3 (neurotrophin-3); NT-4; PAI-1; TGF-α (transforming growth factor-α); TGF-β; and TGF-β3; TRAIL-R4 (TNF-Related Apoptosis-Inducing Ligand Receptor 4).

In certain embodiments, the pro-metastatic factors include, without being limited to, ADAMTS1 (A disintegrin and metalloproteinase with thrombospondin motifs 1); cathepsin S; FGF-2; Follistatin (FST); Galectin-7; GCP-2; GDF-15; IGFBP-6; LIF; MMP-9 (Matrix metallopeptidase 9, also known as 92 kDa gelatinase or gelatinase B (GELB); pro-MMP9; RANK (receptor activator of nuclear factor kB, also known as TRANCE receptor or TNFRSF11A) and its receptor RANKL; RANTES (CCL5); SDF-1 (stromal cell-derived factor 1, also known as CXCL12) and its receptor CXCR4.

The factors may also be anti-tumorigenic factors, e.g., anti-angiogenic, anti-inflammatory and/or anti-proliferative growth factors.

Depending on the cancer therapy modality, the treatment is made in one single session, e.g., surgery, but in most of the modalities such as chemotherapy, radiation therapy, targeted therapy, and immunotherapy, the treatment comprises multiple sessions. In cancer therapy, a cycle of treatment means that the drug is administered to the patient at one point in time (for example, injections over a day or two) and then there is some time of rest (e.g., 1, 2 or 3 weeks) with no treatment. The treatment and rest time make up one treatment cycle. When the patient gets to the end of the cycle, it starts again with the next cycle. A series of cycles of treatment is called a course.

As used herein, "a session of treatment" refers to the "one point in time" when the patient receives the treatment with a drug or another treatment such as radiation at the beginning of a cycle of treatment.

In certain embodiments, the session of treatment is one of multiple sessions of treatment, and the blood sample, preferably blood plasma, is obtained from the cancer patient at about 20, 24 hours or more after said one of multiple sessions of treatment. In certain embodiments, the sample is obtained at 30, 36, 40, 48, 50, 60, 72 hours or more, including up to one to three weeks, after said one of multiple sessions of treatment.

In certain embodiments of the invention, the one of multiple sessions of treatment of the cancer patient is the first session of treatment, when the treatment is started. In this case, the blood sample of step (i) is obtained from the cancer patient at a time point of about 20, 24, 30, 36, 40, 48, 50, 60, 72 hours or more, including up to one week or more, up to two weeks or more or up to three weeks or more, after said first session of treatment, and the reference/baseline blood sample of step (ii) is obtained from the cancer patient at a time point including at about 72 hours or less, including at about 60, 50, 48, 40, 36, 30, or 24, 20 hours or just before said first session of treatment with the cancer therapy.

In certain other embodiments of the invention, the one of multiple sessions of treatment is not the first session of treatment. In this case, the blood sample is obtained from the cancer patient at any time point between two consecutive sessions of treatment, wherein said blood sample is simultaneously the blood sample of step (i) and the reference/baseline blood sample according to step (ii) for the next session assay according to step (i). This means that the reference/baseline sample for this session is the same blood sample obtained from the cancer patient at a time point after the session of treatment that preceded said session that is not the first session. The time between two consecutive sessions of treatment may be from one day to one or 3 weeks, depending on the cancer therapy, and the blood sample is obtained from the cancer patient at about 20, 24, 30, 36, 40, 48, 50, 60, 72 hours or more, including up to one to three weeks or more, after the session of treatment that is not the first session of treatment with the cancer therapy.

The levels of the plurality of factors generated by the host/cancer patient in response to the treatment with the cancer therapy are determined in the blood sample, preferably blood plasma, obtained from the patient post-treatment. The value (factor concentration in pg/mL) obtained for each factor is then compared with the reference level, which is the baseline level of concentration of the same factor determined in a blood sample, preferably blood plasma, obtained previously from the same cancer patient (hereinafter "reference/baseline sample").

In accordance with the invention, the change in the level of one or more of the factors/biomarkers identified in the blood sample obtained from the cancer patient after the treatment compared to the reference/baseline level, is defined by the fold change for each factor. The fold change for each factor is determined by calculating the ratio of treatment:reference/baseline values for the factor.

The fold change is determined for all circulating factors in the patient's blood sample. The prediction of a favorable or a non-favorable response of the cancer patient to the treatment will be based on significant fold changes of one or more, optionally two or more, three or more, four or more, five or more, six or more, seven or more, eight or more, nine or more, ten or more, eleven or more, twelve or more, thirteen or more, fourteen or more, or fifteen or more, twenty or more or twenty-five or more, of the host-driven circulating factors.

In certain embodiments, wherein the fold-change for each of the one or more of the plurality of the host-driven resistance factors denotes an increase (up-regulation) and is considered significant and predictive of a non-favorable response of the cancer patient to the treatment with the cancer therapy if its value is about 1.5 or higher. In certain other embodiments, the fold-change denotes a decrease (down-regulation) and is considered significant and predictive of a favorable response of the cancer patient to the treatment with said cancer therapy if its value is about 0.5 or lower.

In certain embodiments, the session of treatment is the first session of a plurality of sessions of treatment of the cancer patient, when the treatment is started. In this case, if the results show a fold-change of about 1.5 or higher for each of the one or more of the plurality of the host-driven resistance factors, thus denoting an increase (up-regulation) and being considered significant and predictive of a non-favorable response of the cancer patient to the treatment with the cancer therapy, this may assist the medical oncologists treating the patient to decide either not to continue the same cancer treatment or to continue the treatment of the cancer patient with a combination of the same cancer treatment and an agent that blocks the activity of a dominant factor selected among the one or more host-driven resistance factors, or the receptor thereof.

In certain embodiments, the method of the invention is performed for monitoring treatment response in a cancer patient being treated with a cancer therapy. In this case, the session of treatment is one of the sessions of several sessions of treatment, but not the first one. The results will assist the medical oncologist in their decisions if or how to continue the treatment.

In certain embodiments, the cancer therapy is chemotherapy that is typically given in cycles.

In accordance with the invention, chemotherapy is conducted with a single chemotherapy drug (paclitaxel) or with a combination of two drugs (Adriamycin/Cyclophosphamide (AC)) or of three drugs (Folinic acid/Fluorouracil/Oxaliplatin (FOLFOX)).

In certain embodiments, based on Table 3 herein, the circulating factors indicating a host response to chemotherapy include, but are not limited to: 6Ckine; Activin A; Amphiregulin; Angiogenin; Angiopoietin-1; Axl; BDNF; BLC; BMP4; bNGF; Cathepsin S; EGF; ENA-78; Eotaxin; Eotaxin-2; Eotaxin-3; EpCAM; Fcr RIIB/C; FGF-2; FGF-7; Follistatin; Galectin-7; GCP-2; G-CSF; GDF-15; GH; GRO; HB-EGF; HCC-4; I-309; IGFBP-1; IGFBP-6; IL-1α; IL-1β; IL-1ra; IL-2; IL-2 Rb; IL-8; IL-11; IL-12p40; IL-12p70; IL-13 R1; IL-13 R2; IL-16; IL-17; IL-17B; IL-17F; IL-18BPa; IL-23; IL-28A; IP-10; I-TAC; LAP; LIF; Lymphotactin; MCP-1; MCP-2; MCP-3; M-CSF; MDC; MIF; MIG; MIP-1α; MIP-1δ; MIP-3α; MIP-3β; MPIF-1; NGF R; NrCAM; NT-3; NT-4; PAI-1; PARC; PDGF-AA; PDGF-AB; PDGF-BB; PF4; PlGF; PlGF-2; RANTES; Resistin; SCF; SDF-la; ST2; TARC; TECK; TGFα; TGFβ; TGFβ3; Tie-2; TNFα; TNF R1; TRAIL-R4; TREM-1; TLSP; VEGF; VEGF-D; VEGF-R1; VEGF-R2; VEGF-R3.

In one embodiment in accordance with the present invention, the circulating factors shown in Table 3 that were upregulated indicating a host response to chemotherapy with Adriamycin/Cyclophosphamide (AC) or Folinic acid/Fluorouracil/Oxaliplatin (FOLFOX™) include: the pro-angiogenic factors: angiogenin; angiopoietin-1; G-CSF; PDGF-AA; PDGF-AB; PDGF-BB; PlGF; SCF; Tie-2; VEGF A; and VEGF D; the pro-inflammatory and/or chemotactic factors include: BLC (CXCL13); ENA-78 (CXCL5); Eotaxin-3; G-CSF; GDF-15; I-309 (CCL1); IL-1α; IL-1β; IL-1ra; IL-2; IL-8; IL-11; IL-12p40; IL-12p70; IL-13R1; IL-13R2; IL-16; IL-17; IL-17B; IL-17F; IL-18BPa; IL-23; IL-28A; IP-10 (CXCL10); MCP-3; M-CSF; MIF; MIG (CXCL9); MIP-1δ (CCL15); MIP-3α; MIP-3β (CCL19); RANTES (CCL5); SCF; ST2 (IL-1R4); and TARC (CCL17); and the proliferative growth factors include: BDNF; EGF; FGF-7; IGFBP-1; NrCAM; NT-3; NT-4; TGF-α; and TGFβ.

In another embodiment in accordance with the present invention, the circulating factors shown in Table 4 that were upregulated indicating a host response to chemotherapy with paclitaxel or Folinic acid/Fluorouracil/Oxaliplatin (FOLFOX™) include: the pro-angiogenic factors SDF-1 and VEGF-C; the pro-inflammatory and/or chemotactic factors CXCL14 (BRAK); CXCL16; CXCR2 (IL-8 RB); CXCR6; GM-CSF; IL-1alpha; IL-1R4 (ST2); IL-3Ralpha; IL-7Ralpha; IL-9R; IL-1β; IL-11; IL-12p70; IL-15; IL-15Ralpha; IL-17; IL-17R; IL-18R alpha; IL-20; IL-27; IL-28; IL-31; LIF; LIX; LRP-6; MadCAM-1; MCP-1; M-CSF; MIP-1gamma; MIP-2; TACI; and TARC; the proliferative growth factors IGFBP-1; TGF-beta 1; and TGF-beta 2; and the pro-metastatic factor MMP-9.

In another embodiment, the cancer therapy is targeted therapy with the protease inhibitor bortezomib. The circulating factors shown in Table 6 that were upregulated indicating a host response to therapy with bortezomib include the pro-angiogenic factors PlGF-2 and VEGF-D; the pro-inflammatory and/or chemotactic factors CCL28; IL-1alpha; IL-1R4 (ST2); IL-3; IL-5; IL-6; IL-6R; IL-1β; IL-11; IL-12p70; IL-13; IL-17C; IL-17E; IL-31; MCP-1; M-CSF; and MIP-3beta' and the proliferative growth factors IGFBP-1; IGFBP-3; and TGF-beta 3.

In another embodiment, the cancer therapy is radiation therapy. The circulating factors shown in Tables 8A and 8B that were upregulated indicating a host response to radiation therapy include the pro-angiogenic factors angiogenin; angiopoietin-1; Galectin-7; G-CSF; GM-CSF; PDGF-AA; PDGF-BB; PLGF-2; SDF-1, and VEGF-R1; the pro-inflammatory and/or chemotactic factors CD30L, eotaxin-2; galetin-3; IL-1α; IL-4; IL-6; IL-7; IL-9; IL-1β; IL-13; IL-15; IL-17B; IL-17B-R; IL-22; LIX; MCP-1; MCP-5; MIG; MIP-la; RANTES; and TARC; and the proliferative growth factors EGF; and FGF-1.

In another embodiment, the cancer therapy is surgery. The circulating factors shown in Table 9 that were upregulated indicating a host response to surgery include the pro-angiogenic factors angiopoietin-1; PDGF-AA; PDGF-BB; and PLGF-2; and the pro-inflammatory and/or chemotactic factor MCP-1.

Depending on the cancer therapy modality and the treatment protocol, the time between two consecutive sessions of treatment is from one day to 1 or 3 weeks, and the blood sample is obtained from the cancer patient at about 20, 24, 30, 36, 40, 48, 50, 60, 72 hours or more, including up to one to three weeks or more, after the session of treatment that is not the first session of treatment with the cancer therapy. For example, a regular protocol of radiotherapy treatment comprises sessions of 5 times per week in a schedule of 3 to 9, preferably 5-8, weeks, and the blood sample may be obtained at about 20 to 24 hours between two consecutive sessions of treatment. Chemotherapy with Doxorubicin/Cyclophosphamide (AC) or with Paclitaxel™/Doxorubicin/Cyclophosphamide (TAC) is carried out in 4 to 6 cycles with intervals of 14-20 days between the cycles, and the blood sample may be obtained close to about 2-3 weeks between two consecutive sessions of treatment, i.e., just before the next session. Immunotherapy with monoclonal antibodies, e.g., Trastuzumab™ (Herceptin™) is carried out with weekly administrations, and the blood sample may be obtained close to about 1 week between two consecutive sessions of treatment, i.e., just before the next session.

According to the method of the invention for treating a cancer patient with a cancer therapy, if the cancer patient has a non-favorable response to the treatment with said cancer therapy based on the fold change established in (iii) for one or more of the plurality of the host-driven resistance factors, a selection of a dominant factor is made among the one or more factors showing a fold change indicative of said non-favorable response, and the patient is treated with the same cancer therapy in combination with an agent that blocks the selected dominant factor.

The terms "block", "neutralize" or "inhibit" are herein used interchangeably and refer to the capability of an agent of preventing the selected dominant factor from exerting its function/biological activity.

As used herein, the term "dominant factor" denotes a potent factor that may be upstream of a signaling pathway that affects a biological process that is vital for the living cell and living organism. These biological processes include proliferation, inflammation, metastasis, and others, and are made of several signaling pathways ultimately leading to activation or inhibition of the biological process. A "signaling pathway" is a row of events in which proteins in the same pathway transfer signal to each other. After the first protein in a pathway receives a signal, it activates another protein which activates another protein and so forth, ultimately leading to activation of one or more cell functions.

A "dominant factor" may also be a key factor that highly interacts with, and highly affects, many other factors/proteins. According to the invention, the dominant factors are selected based on an algorithm which identifies the protein-protein interactions of factors based on the literature. When a factor has more interactions, it serves as a hub and therefore it is a dominant factor. The term "protein-protein interactions" refers to physical interactions or cross-talk between two or more proteins, resulting in activation or inhibition of signal transduction or protein activity. The term "protein hubs" refers to highly connected proteins that play central and essential role in biological processes and thus may confer the host with resistance, limit or counteract the effectiveness of the treatment of the cancer patient with the cancer therapy modality.

Examples of dominant factors include, without limitation, EGF, EGFR, FGF, IFN-γ, IL-1β, IL-2, IL-6, IL-7, PDGF, TNF-α and VEGF-A. All these factors and other dominant factors appear in the tables of the present application as host response to one or more cancer therapy modalities and are all part of the present invention.

To illustrate their qualifications as dominant factors, the properties of some of these factors is provided herein. Interleukin-1β (IL-1β, IL-1b) is a cytokine member of the IL-1 family, produced by different immune cells including macrophages. It is a potent mediator of the inflammatory response and also known to be involved in several biological processes such as cell proliferation and apoptosis, as well as cell differentiation. IL-10 was mostly investigated as a protein that initiates the pro-inflammatory cascade. It physically interacts with enzymes such as CASP1, IL1RA, IL1R1, CMA1, IL1RB, ILIA, IL1R2; genetically interacts with MAPK8IP2, ZNF675 and UBEN2N; and is co-expressed with A2M, CXCL8, IL18, CAASp1, IL1R1 and others. Thus, IL-10 serves as a hub for interactions with a large number of proteins that affect several biological pathways including cell proliferation, apoptosis and differentiation as well as inflammation and angiogenesis.

Another dominant factor is Interleukin-6 (IL-6), which is a cytokine that acts mainly as a pro-inflammatory factor but also sometimes as an anti-inflammatory factor produced by muscle cells and as a result downregulate a number of pro-inflammatory proteins such as IL-1, IL-10 and TNF-α. IL-6 is involved in a number of biological processes including bone formation, disruption of blood brain barrier, macrophage activation and innate immune system contribution, stimulates the synthesis of neutrophils and B cells, and is also involved in neurological activities such as disorders, stress and depression. IL-6 interacts and affects a large number of proteins: it physically interacts with HRH1, OSM, IL6ST, IL6R and ZBTB16, and was found to be co-expressed with a large number of proteins such as PTPRE, CSF3, CCL2, CXCL8, CXCL3, ICAM1 SELE, NFKBIZ among others. IL-6 is involved in a number of pathways mediated by proteins such as LRPPRC, OSM, PTPRE, PIAS1 and IL6R. As such, IL-6 serves as a dominant factor for a number of biological processes involved in immune cell activity, cell genesis, and cell-cell interactions.

A further dominant factor, vascular endothelial growth factor A (VEGF-A), is a growth factor that stimulates the formation of new blood vessels. It is involved in both angiogenesis (endothelial cell proliferation) as well as vasculogenesis (bone marrow-derived endothelial cell precursors and their differentiation). VEGF is important for embryonic cell development and neuronal development in the fetus, and is involved in leukocyte proliferation and differentiation, inflammation and several diseases such as age-related macular degeneration and the majority of cancers. VEGF-A physically interacts with a large number of proteins such as NRP1, NRP2, KDR, FLT1, PGF, THBS1, SPARC, GCP1 and VEGFC; it is co-expressed with SEMA3F, SHB, THBS1, FLT1 and VEGFC; it is involved with proteins of various pathways including PGF, CD2AP, IQGAP1, NEDD4; and it affects a number of biological processes such as angiogenesis, tumorigenesis, cell viability, proliferation and differentiation. As such, VEGF-A is considered a dominant factor, and vital factor for various biological processes both in normal physiological conditions as well as in disease states.

According to the invention, the selected dominant factor shows a fold change of >1.5 indicative of a non-favorable response of the cancer patient to the treatment with the cancer therapy, and the treatment of the patient with said cancer therapy proceeds in combination with an agent that blocks said dominant factor or the receptor thereof.

The blockade or inhibition of the dominant factor can be done in different ways and by different inhibitors or blocking agents. In certain embodiments, the factor is a cytokine or a growth factor that exerts its biological activity by binding to membrane receptors of target cells, and the blocking agent is an anti-factor monoclonal antibody (mAb) which combines with the factor and thus prevent it from binding to its receptor and thus its capability of exerting is biological function. In this context, the term "neutralizing" the factor is also used. The monoclonal antibodies can be human or humanized monoclonal antibodies, a functional fragment thereof, a monobody or a conjugated antibody. Examples are Infliximab™ and Adalimumab™, humanized mAbs directed against TNF-α.

In certain embodiments, the agent that blocks the factor is a mAb which combines with the factor's receptor, thus preventing the factor's binding to the receptor. Examples are the anti-IL-2R mAbs Basiliximab™ and Daclizumab™.

In certain embodiments, the agent that blocks the factor is a decoy receptor which is a receptor that is able to recognize and bind specific growth factors or cytokines efficiently, but is not structurally able to signal or activate the intended receptor complex. It acts as an inhibitor, binding a ligand and keeping it from binding to its regular receptor. Examples of decoy receptors are IL-IR2, that binds IL-1β and IL-1β, and inhibits their binding to IL-R1; VEGFR-1 that inhibits the activity of VEGF-VEGFR-2 axis by sequestering VEGF, thus preventing VEGFR-2 from binding to VEGF and activate VEGF signaling; the drug Etanercept (trade name Enbrel), a fusion protein comprising the sequence of the soluble T-NF-R2, which is a receptor that also binds to TNF-α, and inhibits TNF-α of binding to TNF-R1.

In another aspect, the present invention relates to a cancer drug for use in the treatment of cancer in a patient non-responsive to said drug, comprising administering a therapeutically effective amount of the drug in combination with a therapeutically effective amount of an agent that blocks the activity of a dominant factor, or the receptor thereof, the dominant factor being selected among the plurality of host-driven resistance factors generated in response to treatment of the cancer patient with the cancer drug, the plurality of host-driven resistance factors having a fold-change predictive of a non-favorable response of the cancer patient to the treatment with the cancer drug, wherein the fold change is established by comparing: (i) the level of the host-driven resistance factors in a blood sample selected from blood plasma, whole blood, blood serum or peripheral blood mononuclear cells, obtained from the cancer patient after a session of treatment with the cancer drug, with (ii) a reference level obtained from a blood sample of the same type of (i), obtained from the cancer patient before said session of treatment with the cancer drug.

According to this aspect of the invention, when the cancer therapy is radiotherapy and no drugs are used, the invention relates to an agent that blocks the activity of a dominant factor, or of the receptor thereof, for use in radiotherapy treatment of cancer in a patient non-responsive to radiotherapy, comprising administering a therapeutically effective amount of the agent in combination with therapeutic doses of radiation, the dominant factor being selected among the plurality of host-driven resistance factors generated in response to treatment of the cancer patient with radiotherapy, the plurality of host-driven resistance factors having a fold-change predictive of a non-favorable response of the cancer patient to the treatment with the radiotherapy, wherein the fold change is established by comparing: (i) the level of the host-driven resistance factors in a blood sample selected from blood plasma, whole blood, blood serum or peripheral blood mononuclear cells, obtained from the cancer patient after a session of treatment with the radiotherapy, with (ii) a reference level obtained from a blood sample of the same type of (i), obtained from the cancer patient before said session of treatment with the radiotherapy.

Preferably, the blood samples of steps (i) and (ii) are both blood plasma.

The session of treatment with the cancer drug or with the radiotherapy may be the first session of treatment with the cancer drug or the radiotherapy or may be one of multiple sessions of treatment that is not the first session of treatment with the cancer therapy or the radiotherapy as described hereinbefore for the method of treatment and the blood samples are obtained from the cancer patient at the time points as described hereinbefore.

The fold-change for each of the one or more of the plurality of host-driven resistance factors and for the dominant factor selected therefrom is about 1.5 or higher denoting an increase/up-regulation and is considered significant and predictive of a non-favorable response of the cancer patient to the treatment with the cancer drug or the radiotherapy. As described hereinbefore, the host-driven resistance factors generated by the cancer patient in response to treatment with the cancer drug or the radiotherapy are molecular factors including cytokines, chemokines, growth factors, enzymes and soluble receptors, that may be pro-tumorigenic or pro-metastatic factors, and the pro-tumorigenic factors may be pro-angiogenic, pro-inflammatory/chemotactic or proliferative growth factors.

According to the invention, the cancer drug to is for use in a cancer therapy modality including chemotherapy, targeted cancer therapy, hormonal therapy, thermotherapy, and combinations thereof, all as described hereinbefore.

In one embodiment, the dominant factor is IL-6 that may be blocked with: (a) an agent that blocks the activity of IL-6, said agent including a human or humanized monoclonal antibody such as Siltuximab™, Clazakizumab™, Olokizumab™, Elsilimomab™, or Sirukumab™; or (b) an agent that blocks the receptor IL-6R, said agent including a human or humanized monoclonal antibody such as Tocilizumab™, Sarilumab™ or a nanobody such as Vobarilizumab™. In one embodiment, the cancer therapy is chemotherapy and the cancer patient is treated with a chemotherapy drug in combination an anti-IL-6 or an anti-IL-6R agent. In one embodiment, the cancer drug is the chemotherapy drug Adriamycin™ (doxorubicin) for treatment of breast cancer, and the agent that blocks the IL-6 is a human or humanized anti-IL-6 monoclonal antibody. The Adriamycin and the monoclonal antibody may be administered concurrently, e.g., by infusion, or sequentially, in either order.

In one embodiment, the dominant factor is the dominant factor is IL-7 and the cancer therapy is radiotherapy. In this case, the cancer patient is treated with radiotherapy in combination with an agent that blocks the activity of IL-7 or of IL-7 receptor (IL-7R). In one embodiment, the radiotherapy is for treatment of colon cancer, and the agent that blocks the IL-7 is an anti-IL-7R human or humanized monoclonal antibody.

In certain embodiments, the dominant factor is IL-10 that may be blockaded by an agent that blocks the activity of IL-1β or blocks its receptor IL-1R, said agent including: (a) an IL-1 receptor antagonist (IL-1Ra), e.g. Anakinra™, a recombinant form of the physiologic human protein IL-1Ra which binds the IL-1 type 1 receptor (IL-1R) without causing signaling and thereby prevents activation by the agonistic ligands IL-1α and IL-1β; (b) a soluble decoy IL-1 type II receptor, e.g., Rilonacept™; (c) an anti-IL-10 mAb, e.g., Canakinumab™, Gevokizumab™, LY2189102 or Lutikizumab™; (d) an anti-IL-1R mAb, e.g., MEDI-8968 or GSK1827771; (e) an IL-10-converting enzyme (ICE) inhibitor, e.g., Pralnacasan™ or Belnacasan™; and (f) an IL-10 vaccine. In one embodiment, the cancer therapy is chemotherapy, for example, with a combination of Adriamycin™ and cyclophosphamide (A/C) for treatment of breast cancer, and the agent that blocks the IL-10 or its receptor may be IL-1Ra Anakinra™, where the A/C combination and the Anakinra™ may be administered concurrently or sequentially, in either order.

In certain embodiments, the dominant factor is VEGF-A, and the agent that blocks the factor is bevacizumab (Avastin™), a humanized mAb. In other embodiments, the factor is EGFR and the agent that blocks the receptor is Cetuximab (Erbitux™) or Panitumumab.

According to the invention, the cancer to be treated is a primary or a metastatic cancer including bladder, bone, breast, brain, cervical, colon, colorectal, esophageal, gastric cancer, gastrointestinal, glioblastoma, head and neck, head and neck squamous cell cancer, hepatocellular cancer, kidney, liver, lung including small cell lung cancer and non-small cell lung cancer (NSCLC, melanoma, nasopharyngeal, ovarian, pancreas, penile, prostate, skin, testicular, thymus, thyroid, urogenital, or uterine cancer, leukemia, lymphoma, multiple myeloma and sarcoma.

The invention will now be illustrated by the following non-limiting Examples.

EXAMPLES

Materials and Methods (i) Materials:

The following antibodies were purchased from BioXcell: InVivoMAb anti-mouse-PD-1 (cat. #BE0146); InVivoPlus anti-mouse-PD-L1 (cat. #BPO101); InVivoMAb Isotype control IgG2b antibody (cat. #BE0090); InVivoMAb anti-mouse-IL-6 (cat. #BE0046); InVivoMAb Isotype control IgG2b antibody (cat. #BE0090); and InVivoMAb anti-mouse-IL-7R (cat. #BE002). FOLFOX™ (14 mg/kg oxaliplatin (Medac Pharma); 50 mg/kg 5-fluorouracil (Ebewe Pharma); 30 mg/kg folinic acid/leucovorin (ABIC)); Paclitaxel™ (BioAvenir Ltd.); Doxorubicin (DOX); Bortezomib™, Selleckchem™ (cat. #S1013).

(ii) Cancer Cell Cultures:

Murine EMT6 breast carcinoma cells were purchased from the American Type Culture Collection (ATCC, USA). The cells were passaged in culture for no more than 4 months after being thawed from authentic stocks and were regularly tested to be *mycoplasma*-free (EZ-PCR *mycoplasma* test kit, Biological industries). Cells were cultured in Dulbecco's modified eagle medium (DMEM) supplemented with 10% fetal bovine serum (FBS), 1% L-glutamine, 1% sodium-pyruvate and 1% penicillin-streptomycin (Biological Industries, Israel), at 37° C. in 5% $CO_2$.

(iii) Plasma Isolation Procedure:

Plasma was isolated by centrifugation of the whole blood at 1300 g for 10 minutes at room temperature. Supernatant representing the plasma was aliquoted and stored at −80° C. until further use.

(iv) Animal Treatment Protocols and Tumor Models:

BALB/c mice were purchased from Envigo, Israel, and experiments were performed in accordance with the animal ethic committee at the Technion (Haifa, Israel).

To determine whether blocking host-derived IL-6 improves the efficacy of Doxorubicin (DOX) treatment, 7 weeks old female BALB/c mice were orthotopically injected with $5 \times 10^5$ EMT6 murine breast carcinoma cells into the mammary fat pad. Tumor size was assessed regularly with Vernier calipers using the formula width$^2 \times$length$\times 0.5$. When tumors reached a size of 100 mm$^3$, mice (n=5) were intraperitoneally (IP) injected with 240 μg DOX, 200 μg anti-IL-6 (every 3 days, a total of 3 injections), or a combination of DOX with anti-IL-6. Control mice (n=4) were left untreated. Tumor growth was monitored regularly and when tumor size reached 1500 mm$^3$, mice were sacrificed.

For the experiment testing the treatment with radiation in combination with anti-IL-7, CT26 cells ($2 \times 10^6$) were subcutaneously injected to the flanks of 6 weeks old female BALB/c mice. Tumor size was assessed and when tumors reached a size of 150 mm$^3$, mice (n=6) were locally irradiated with a total of 2Gy to the flank, IP injected with 200 μg anti-IL-7 or treated with radiation in combination with anti-IL-7 every 3-4 days (a total of 4 injections). Tumors growth was monitored regularly and when reached a size of ~1000 mm$^3$ mice were sacrificed.

(v) IL-6 Quantification Using ELISA:

For determination of IL-6 expression following DOX treatment, 7 weeks old naïve female BALB/c mice (n=3) were IP injected with 240 μg DOX. Control mice (n=3) were left untreated. One day after the injection, mice were bled by cardiac puncture and blood was collected into EDTA-coated tubes. Plasma was isolated by centrifugation of the whole blood at 1300 g for 10 minutes at room temperature. Supernatants (representing the plasma samples) were collected and the level of IL-6 in the plasma was determined by ELISA (IL-6 Quantikine ELISA Kit, R&D systems) according to the manufacturer's instruction.

(vi) Protein Expression Profiling Using Protein Array:

Determination of proteins expression using protein arrays was performed according to the manufacturer's instructions. For the membrane-based array, pixel densities on developed X-ray films were analyzed using transmission mode densitometer and image analysis software. For the glass slide-based arrays, the fluorescent readout was detected by a laser fluorescent scanner. In all cases, data was normalized and the fold changes for each factor on the arrays were determined by calculating the ratio of treated:control values. Factors exhibiting a fold change of more than 1.5 or less than 0.5 were defined as being up- or down-regulated, respectively, in response to therapy.

(vii) Statistical Analysis:

Data is expressed as mean±standard deviation (SD). For the quantification by ELISA, the statistical significance of differences was assessed by two tailed unpaired T-test. For the tumor growth assessment, the statistical significance of differences was assessed by multiple T-test. For the survival analysis differences were assessed by Log-rank Mantle-Cox. Differences between all groups were compared with each other and were considered significant at p values below 0.05.

Example 1. The Effect of Chemotherapy on Circulating Pro-Tumorigenic Factors—a Protein Profiling Approach in Humans In order to define a profile of circulating factors indicative of a pro-tumorigenic host response to chemotherapy in human cancer patients, a total of 16 breast and 19 colorectal cancer patients were recruited to this study. All breast cancer patients received Adriamycin/Cyclophosphamide (AC) chemotherapy, and all colorectal cancer patients received Folinic acid/Fluorouracil/Oxaliplatin (FOLFOX™) chemotherapy according to standard regimens at HaEmek Medical Center, Afula, Israel. Blood samples from the patients were drawn into EDTA tubes at 2 time points: i) before receiving the first dose of chemotherapy (baseline); ii) 24 hours after receiving the first dose of chemotherapy (post-treatment), and plasma was isolated. Baseline and post-treatment samples (100 μl) were applied to 4 glass slide-based antibody arrays (RayBiotech; Human Cytokine Array GS2000 and GS4000) according to the manufacturer's instruction. A total of 160 factors were included in the screen, with each array detecting 40 non-overlapping factors. The antibody arrays used, and their respective list of cytokines, enzymes and growth factors, are shown in Table 1 hereinafter. Normalized data was then analyzed to identify factors whose circulating levels were changed 24 hours after chemotherapy administration. Specifically, the fold change was determined for each factor by calculating the ratio of post-treatment: baseline values. Candidate factors were chosen based on defined thresholds of fold change. Factors exhibiting a fold change of more than 1.5 or less than 0.5 were defined as being up- or down-regulated, respectively, in response to chemotherapy. The average fold change for up- and down-regulated factors was calculated and is shown in Table 2. Many of these factors are key players in pro-tumorigenic and pro-metastatic processes such as angiogenesis, inflammation, chemotaxis and proliferation. Importantly, each patient exhibited a unique profile of factors. A list of factors found to be up- or down-regulated in response to either chemotherapy type in more than 18% of patients is shown in Table 3.

The upregulated pro-angiogenic factors in Table 3 include: angiogenin; angiopoietin-1; G-CSF; PDGF-AA; PDGF-AB; PDGF-BB; PlGF; SCF; Tie-2; VEGF A; and VEGF D. The up-regulated pro-inflammatory and/or chemotactic factors include: BLC (CXCL13); ENA-78 (CXCL5); Eotaxin-3; G-CSF; GDF-15; I-309 (CCL1); IL-1α; IL-1β; IL-1ra; IL-2; IL-8; IL-11; IL-12p40; IL-12p70; IL-13R1; IL-13R2; IL-16; IL-17; IL-17B; IL-17F; IL-18BPa; IL-23; IL-28A; IP-10 (CXCL10); MCP-3; M-CSF; MIF; MIG (CXCL9); MIP-1δ (CCL15); MIP-3α; MIP-3β (CCL19); RANTES (CCL5); SCF; ST2 (IL-1R4); and TARC (CCL17). The upregulated proliferative growth factors include: BDNF; EGF; FGF-7; IGFBP-1; NrCAM; NT-3; NT-4; TGF-α; and TGFβ.

Example 2. The Effect of Chemotherapy on Circulating Host-Derived Pro-Tumorigenic Factors—a Protein Profiling Approach in Mice To identify host-derived circulating factors whose levels change in response to chemotherapy, a protein array-based screens were performed using plasma from naïve (non-tumor bearing) mice that were treated with different chemotherapy types. The use of naïve mice allows identification of factors specifically generated by the host in response to chemotherapy, independent of tumor presence. To this end, naïve 8-10 week old female BALB/c mice (n=5 mice per group) were treated with either FOLFOX™ (14 mg/kg oxaliplatin (Medac Pharma, Chicago, IL, US); 50 mg/kg 5-fluorouracil (Ebewe Pharma, Vienna, Austria); 30 mg/kg folinic acid/leucovorin (ABIC, Israel)) or Paclitaxel™ (Bio-Avenir Ltd., Israel; 25 mg/kg) chemotherapy administered as a single bolus intraperitoneal injection. Control mice (n=5) were injected with vehicle control. Twenty-four hours after treatment administration, mice were sacrificed, plasma was isolated and pooled per group. Control and treatment plasma samples were applied to a glass slide-based Mouse L308 Array (RayBiotech; Cat no: AAM-BLG-1-2) according to the manufacturer's instruction to screen a total of 308 factors. The full list of cytokines, enzymes and growth factors detected by the array is shown in Table 4. Normalized data was analyzed to identify factors whose circulating levels were changed in response to the two chemotherapy types. Specifically, the fold change was determined for each factor by calculating the ratio of treated:control values. Factors exhibiting a fold change of more than 1.5 or less than 0.5 were defined as being up- or down-regulated, respectively, in response to chemotherapy. These factors, and their respective fold changes in response to each chemotherapy type (Paclitaxel™, FOLFOX™), are listed in Table 5. The data demonstrate that FOLFOX™ and Paclitaxel™ chemotherapies induce different profiles of up- and down-regulated factors. Many of the factors that were upregulated (a fold change of more than 1.5) in response to the chemotherapies are key players in pro-tumorigenic and pro-metastatic processes such as angiogenesis, inflammation, chemotaxis and proliferation. Upregulated pro-angiogenic factors include: SDF-1 and VEGF-C. Up-regulated pro-inflammatory and/or chemotactic factors include: CXCL14 (BRAK); CXCL16; CXCR2 (IL-8 RB); CXCR6; GM-CSF; IL-1alpha; IL-1R4 (ST2); IL-3Ralpha; IL-7Ralpha; IL-9R; IL-1β; IL-11; IL-12p70; IL-15; IL-15Ralpha; IL-17; IL-17R; IL-18R alpha; IL-20; IL-27; IL-28; IL-31; LIF; LIX; LRP-6; Mad-CAM-1; MCP-1; M-CSF; MIP-1gamma; MIP-2; TACI; and TARC. Upregulated proliferative growth factors include: IGFBP-1; TGF-beta 1; and TGF-beta 2. Upregulated pro-metastatic factors include: MMP-9.

Example 3. The Effect of Bortezomib on Circulating Host-Derived Pro-Tumorigenic Factors—a Protein Profiling Approach in Mice The molecularly targeted drug, bortezomib (Velcade™), is a proteasome inhibitor used for the treatment of multiple myeloma and mantle cell lymphoma. To identify host-derived circulating factors whose levels change in response to bortezomib, a protein array-based screen using plasma from naïve (non-tumor bearing) mice that were treated with bortezomib was performed. The use of naïve mice allows identification of factors specifically generated by the host in response to bortezomib, independent of tumor presence.

Naïve 8-10 week old female BALB/c mice (n=5 mice per group) were intravenously injected with 1 mg/kg bortezomib and control mice were injected with vehicle control. Twenty-four hours after treatment administration, mice were sacrificed, blood was collected, and plasma was isolated and pooled per group. Plasma samples were applied to a glass slide-based Mouse L308 Array (RayBiotech; Cat no: AAM-BLG-1-2), the same array used in Example 2, according to the manufacturer's instruction to screen a total of 308 factors (see Table 4). Normalized data was analyzed to identify factors whose circulating levels were changed in response to bortezomib treatment, by calculating the fold change for each factor (the ratio of treated:control values). The factors and their respective fold changes are listed in Table 6. Factors exhibiting a fold change of more than 1.5 or less than 0.5 were defined as being up- or down-regulated, respectively, in response to bortezomib. Many of the factors that were upregulated in response to bortezomib are key players in pro-tumorigenic and pro-metastatic processes such as angiogenesis, inflammation, chemotaxis and proliferation. Upregulated pro-angiogenic factors include: PlGF-2 and VEGF-D. Up-regulated pro-inflammatory and/or chemotactic factors include: CCL28; IL-1alpha; IL-1R4 (ST2); IL-3; IL-5; IL-6; IL-6R; IL-1β; IL-11; IL-12p70; IL-13; IL-17C; IL-17E; IL-31; MCP-1; M-CSF; and MIP-3beta. Upregulated proliferative growth factors include: IGFBP-1; IGFBP-3; and TGF-beta 3.

Example 4. The Effect of Radiotherapy on Circulating Host-Derived Pro-Tumorigenic Factors—a Protein Profiling Approach in Mice To identify host-derived circulating factors whose levels change in response to radiotherapy, protein array-based screens using plasma from naïve (non-tumor bearing) irradiated mice was performed. The use of naïve mice allows identification of factors specifically generated by the host in response to radiotherapy, independent of tumor presence.

In the first experiment, naïve 8-10 weeks old female BALB/c mice (n=5 mice per group) were locally irradiated to the abdominal cavity with a linear accelerator 6 MeV electron beam using Elekta Precise (ElektaOncology Systems) at a dose rate of 40 cGy per minute, for a total dose of 2Gy at room temperature. Control mice were not irradiated. Twenty-four hours after radiation, mice were sacrificed, blood was collected, and plasma was isolated and pooled per group. Control and treatment plasma samples were applied to a membrane-based Proteome Profiler Mouse Angiogenesis Array (R&D Systems; Cat no: ARY015) to screen a total of 53 factors. A full list of cytokines, enzymes and growth factors detected by the array is shown in Table 7. Pixel densities on developed X-ray films were analyzed using transmission mode densitometer and image analysis software. Normalized data was analyzed to identify factors whose circulating levels were changed in response to radiation. Specifically, the fold change was determined for each factor by calculating the ratio of treated:control values. Factors exhibiting a fold change of more than 1.5 or less than 0.5 were defined as being up- or down-regulated, respectively, in response to radiation. These factors and their respective fold changes are listed in Table 8A. In the second experiment, naïve 6 weeks old female BALB/c mice (n=5) were irradiated (according to the same protocol described in the first experiment). Control mice (n=5) were not irradiated. Twenty-four hours after radiation, mice were sacrificed, blood was collected, and plasma was isolated. The unpooled plasma samples (n=5 samples per group) were applied to glass slide-based Quantibody Mouse Cytokine Arrays (RayBiotech, Cat no: QAM-CAA-4000), according to the manufacturer's instruction, to screen a total of 200 proteins. The full list of cytokines, enzymes and growth factors measured by the array are shown in Table 12. The fluorescent readout was detected by a laser fluorescent scanner. Normalized data was averaged (per group) and analyzed to identify factors whose circulating levels were changed in response to radiation. The fold changes were determined for each factor on the protein array by calculating the ratio of treated:control values. Factors exhibiting a fold change of more than 1.5 or less than 0.5 were defined as being up- or down-regulated, respectively, in response to radiation. These factors and their respective fold changes are listed in Table 8B. Many of the factors that were upregulated in response to radiotherapy are key players in pro-tumorigenic and pro-metastatic processes such as angiogenesis, inflammation, chemotaxis and proliferation. Upregulated pro-angiogenic factors include: angiogenin; angiopoietin-1; PDGF-AA; PDGF-BB; PLGF-2; VEGF-R1; G-CSF; Galectin-7 and SDF-1. Up-regulated pro-inflammatory and/or chemotactic factors include: IL-1β; MCP-1; TARC; RANTES; MIP-la; MIG; MCP-5; LIX; IL-9; IL-7; IL-6; IL-4; IL-22; IL-1α; IL-17B; IL-17B-R; IL-15; IL-13; GM-CSF; Galectin-3; Eotaxin-2 and CD30L. Upregulated proliferative growth factors include: EGF; and FGF-1.

Example 5. The Effect of Surgery on Circulating Host-Derived Pro-Tumorigenic Factors—a Protein Profiling Approach in Mice To identify host-derived circulating factors whose levels change in response to surgery, a protein array-based screen using plasma from naïve (non-tumor bearing) mice that underwent a surgical procedure was performed. The use of naïve mice allows identification of factors specifically generated by the host in response to surgery, independent of tumor presence.

Naïve 8-10 weeks old female BALB/c mice (n=5 mice per group) underwent a surgical procedure. Specifically, a 1 cm incision in the abdominal region of mice was made, followed by suturing. Control mice were not operated. Twenty-four hours after the surgical procedure, mice were sacrificed, blood was collected, and plasma was isolated and pooled per group. Control and post-surgery plasma samples were applied to a membrane-based Proteome Profiler Mouse Angiogenesis Array™ (R&D Systems; Cat no: ARY015), the same array used in Example 4 (see Table 7) to screen a total of 53 factors. The array was developed, and normalized data was analyzed to identify factors whose circulating levels were changed in response to surgery. Specifically, the fold change was determined for each factor by calculating the ratio of post-surgery:control values. Factors exhibiting a fold change of more than 1.5 or less than 0.5 were defined as being up- or down-regulated, respectively, in response to surgery. These factors and their respective fold changes are listed in Table 9. Many of the factors that were upregulated after surgery are key players in pro-tumorigenic and pro-metastatic processes such as angiogenesis, inflammation, and chemotaxis. Upregulated pro-angiogenic factors include angiopoietin-1; PDGF-AA; PDGF-BB; and PLGF-2. Up-regulated pro-inflammatory and/or chemotactic factors include: MCP-1.

Example 6. The Effect of Immune Checkpoint Inhibitor Therapy on Circulating Host-Derived Pro-Tumorigenic Factors—a Protein Profiling Approach in Mice To identify host-derived circulating factors whose levels change in response to immune checkpoint inhibitor therapy, 3 protein array-based screens using naïve (non-tumor bearing) mice were performed. The use of naïve mice allows identification of factors specifically generated by the host in response to therapy, independent of the tumor.

In the first screen, naïve 8-10 weeks old female BALB/c mice (n=3 mice per group) were intraperitoneally injected with 200 μg anti-PD-1 every other two days over a period of 1 week (3 injections in total). Control mice were similarly injected with 200 μg IgG antibody. One week after the first injection, mice were sacrificed, blood was collected, and plasma was isolated and pooled per group. Plasma samples were applied to a membrane-based Proteome Profiler Mouse XL Cytokine Array™ (R&D Systems; Cat no: ARY028) to screen a total of 111 factors. A full list of cytokines, enzymes and growth factors detected by the array is shown in Table 10. The array was developed, and normalized data was analyzed to identify factors whose circulating levels were changed in response to anti-PD-1 therapy. Specifically, the fold change was determined for each factor by calculating the ratio of treatment:control values. Factors exhibiting a fold change of more than 1.5 or less than 0.5 were defined as being up- or down-regulated, respectively, in response to anti-PD-1 therapy. These factors and their respective fold changes are listed in Table 11. Many of the factors that were upregulated in response to anti-PD-1 therapy are key players in pro-tumorigenic and pro-metastatic processes such as angiogenesis, inflammation, chemotaxis and proliferation. Upregulated pro-angiogenic factors include: G-CSF; GM-CSF; and PDGF-BB. Up-regulated pro-inflammatory and/or chemotactic factors include: CCL17/TARC; CCL5/RANTES; G-CSF; GM-CSF; IFN-gamma; IL-1Ralpha; IL-2; IL-6; IL-7; IL-1β; IL-12p40; IL-13; IL-33; and M-CSF. Upregulated proliferative growth factors include: FGF-21; Gas6; and HGF. Upregulated pro-metastatic factors include: MMP-9.

In the second screen, naïve 8-10 week old female BALB/c, male BALB/c, female C57Bl/6 or male C57Bl/6 mice (n=7 mice per group) were intra-peritoneally injected with 200 μg anti-PD-L1 or control IgG antibodies every other day over a period of 1 week (3 injections in total). Twenty-four hours after the last administration, mice were sacrificed, blood was drawn, and plasma was isolated. Plasma samples from each group were pooled and applied to a glass slide-based Quantibody Mouse Cytokine Array™ (RayBiotech, Cat no: QAM-CAA-4000) according to the manufacturer's instruction to screen a total of 200 factors. A full list of cytokines, enzymes and growth factors detected by the array is shown in Table 12. The fold changes were determined for each factor on the protein array by calculating the ratio of treated:control values. Factors exhibiting a fold change of more than 1.5 or less than 0.5 were defined as being up- or down-regulated, respectively, in response to anti-PD-L1 therapy. These factors and their respective fold changes are listed in Table 13. The data demonstrate that the profiles of up- and down-regulated factors do not completely overlap when comparing between the different mouse strains or when comparing between males and females of the same strain. This suggests that the response to anti-PD-L1 therapy is genotype-dependent and can therefore be tested in a personalized manner. Many of the factors that were upregulated in response to anti-PD-L1 therapy are key players in pro-tumorigenic and pro-metastatic processes such as inflammation, chemotaxis and proliferation. Upregulated pro-angiogenic factors include: G-CSF; and SCF. Upregulated pro-inflammatory and/or chemotactic factors include: Eotaxin-2; G-CSF; IL-1ra; IL-6; IL-7; IL-33; I-TAC; MadCAM-1; MCP-5; SCF; and TAC. Upregulated proliferative growth factors include: amphiregulin; Axl; EGF; and HGF. Upregulated pro-metastatic factors include: ADAMTS1 and pro-MMP9.

To gain insight into which host cell types secrete these pro-tumorigenic factors, we performed a similar screen, comparing between BALB/c and SCID mice treated with anti-PD-1 or control IgG antibodies. SCID mice carry the severe combined immune deficiency (SCID) mutation on the BALB/c background, and therefore lack functional adaptive immune cell types (B cells and T cells). Naïve 8-10 week old female BALB/c or SCID mice (n=7 mice per group) were intraperitoneally injected with 200 g anti-PD-1 or control IgG antibodies every other day over a period of 1 week (3 injections in total). Twenty-four hours after the last administration, mice were sacrificed, blood was drawn and plasma was isolated. Plasma samples from each group were pooled and applied to a glass slide-based Quantibody Mouse Cytokine Array™ (RayBiotech, Cat no: QAM-CAA-4000), the same array used in the second screen above (see Table 12), according to the manufacturer's instruction to screen a total of 200 factors. The fold changes were determined for each factor on the protein array by calculating the ratio of treated:control values. Factors exhibiting a fold change of more than 1.5 or less than 0.5 were defined as being up- or down-regulated, respectively, in response to anti-PD-1 therapy. These factors and their respective fold changes are listed in Table 14. Several factors were found to be upregulated in response to anti-PD-1 therapy, some of which were specific to BALB/c and not SCID mice, e.g., ADAMTS1; amphiregulin, I-TAC and SCF. These results suggest that these specific factors are secreted by cells of the adaptive immune system in response to anti-PD-1 therapy.

Example 7. Blocking of Chemotherapy-Induced IL-6 Improves Treatment Efficacy

As shown in Table 2A, IL-6 was among the factors in the protein array found to be induced in response to chemotherapy in breast and colon cancer patients. IL-6 is known to be involved in number of biological processes crucial for tumor development including proliferation, angiogenesis, inflammation, differentiation and resistance to apoptosis. In addition, IL-6 is a pro-inflammatory cytokine that has been described as a prognostic factor in cancer. Since IL-6 is located at the top of the pro-inflammatory cascade and has been demonstrated to correlate with metastasis it is considered as a dominant factor with pro-tumorigenic and pro-metastatic activities. For this reason, it was tested whether blocking of host-derived IL-6 improves the efficacy of chemotherapy treatment.

To investigate the effect of chemotherapy on the level of IL-6 in the circulation, naïve 7-weeks old female BALB/c mice were IP injected with 240 μg DOX (doxorubicin, Adriamycin™) or were left untreated (control mice). One day after the injection, the level of IL-6 in the plasma was determined by ELISA. The results presented in FIG. 1A show that the plasma level of IL-6 was increased by 22-fold in response to DOX therapy compared to control.

Figure 1B:
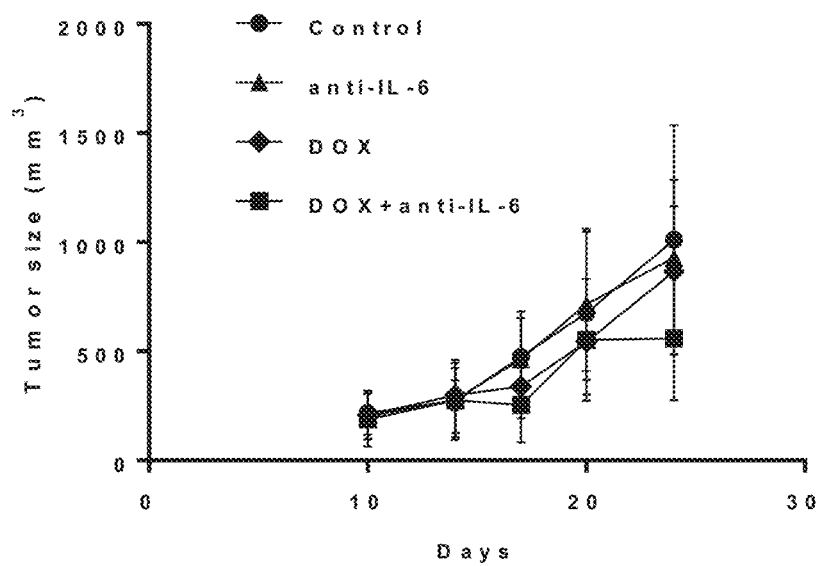

To determine whether blocking host-derived IL-6 (upregulated in response to DOX) improves the efficacy of the treatment, BALB/c mice were orthotopically injected with EMT6 cells into the mammary fat pad. Upon tumor size of 100 mm$^3$, mice were injected with 240 μg DOX, 200 μg anti-IL-6 mAb or a combination of DOX with anti-IL-6 mAb. Control mice were left untreated. When tumors reached a size of 1500 mm$^3$, mice were sacrificed. FIG. 1B demonstrates enhanced anti-tumor effect of the combined DOX and anti-IL-6 mAb treatment compared to the control, DOX monotherapy and anti-IL-6 mAb monotherapy. These results show that blocking chemotherapy-induced IL-6 improves treatment outcome.

Example 8. Blocking of Radiation-Induced IL-7 Inhibits Primary Tumor Growth and Improves Mice Survival As previously presented in Table 8B, IL-7 was among the factors whose expression was altered in response to treatment with radiotherapy. An increase of ~6 fold (p<0.0001) in IL-7 concentration in the radiation-treated compared to control mice was observed. Of note, since this experiment was performed using naïve mice, it demonstrates that IL-7 is produced by host cells in response to radiation, independent of tumor presence. Many studies suggested a potential protumorigenic role for IL-7, by promoting proliferation and survival of cancer cells and involvement in cancer invasion and migration, proposing that its expression is indicative of non-responsiveness to cancer treatment, and thus its inhibition may improve treatment efficacy.

To study whether blocking of host-derived IL-7 upregulated in response to radiotherapy improves the efficacy of the treatment, BALB/c mice were subcutaneously injected with CT26 murine colon cancer cells into the flanks. When tumors reached a size of 150 mm$^3$, mice were either exposed to 2Gy radiation in the abdominal region, intraperitoneally injected with anti-IL-7R mAb or treated with a combination of radiation and anti-IL-7R mAb.

Figure 2A:
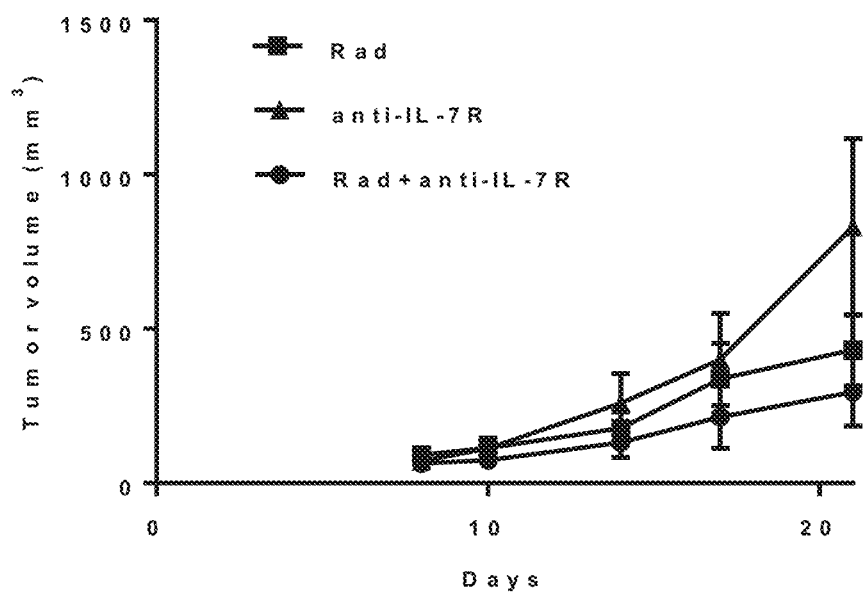
FIGS. 2A-2B show the effect of blocking host-induced IL-7 on radiotherapy treatment efficacy. Treatment with radiotherapy in combination with anti-IL-7R has greater anti-tumor (FIG. 2A) and pro-survival effects (FIG. 2B) than radiotherapy or anti-IL-7R treatments alone.

Tumors growth was monitored regularly. The results presented in FIG. 2A demonstrate that combined treatment of radiation and anti-IL-7R mAb resulted in greater inhibition of primary tumor growth compared to radiation or anti-IL-7R mAb alone (p=0.49 and 0.68 respectively).

Figure 2B:
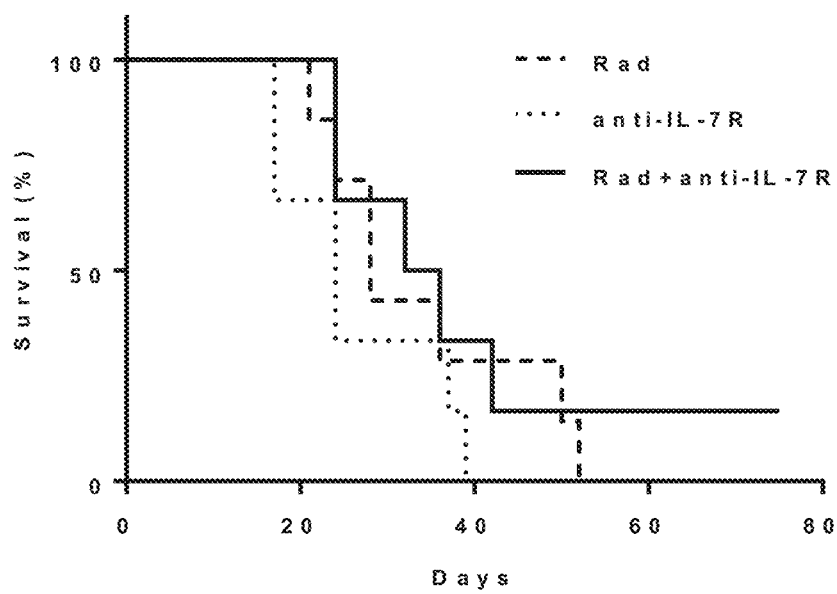

Blocking host-derived IL-7 in combination with radiotherapy did not only improve tumor burden but also improved mice survival. As shown in FIG. 2B, mice treated with radiation in combination with anti-TL-7R mAb exhibited enhanced survival rate (median survival of 34 days) compared to mice treated with either radiation or anti-IL-7R mAb alone (median survivals of 28 and 24 respectively), p=0.634 and 0.198, respectively.

TABLE 1

List of 160 factors participating in the antibody array screen performed with plasma from human subjects receiving chemotherapy

| Human Cytokine Array GS2000 ™; GSH-CHE-1 chip (RayBiotech) | Human Cytokine Array GS2000 ™; GSH-GF-1 chip (RayBiotech) | Human Cytokine Array GS2000 ™; GSH-INF-3 chip (RayBiotech) | Human Cytokine Array GS4000 ™; GSH-CYT-1 chip (RayBiotech) |
|---|---|---|---|
| 6Ckine | AR | BLC | Activin A |
| Axl | BDNF | Eotaxin | AgRP |
| BTC | bFGF | Eotaxin-2 | ANG |
| CCL28 | BMP-4 | G-CSF | ANG-1 |
| CTACK | BMP-5 | GM-CSF | Angiostatin |
| CXCL16 | BMP-7 | I-309 | CathepsinS |
| ENA-78 | b-NGF | ICAM-1 | CD 40 |
| Eotaxin-3 | EGF | ICAM-1 | Cripto-1 |
| GCP-2 | EGF R | IL-1a | DAN |
| GRO | EG-VEGF | IL-1b | DKK-1 |
| HCC-1 | FGF-4 | IL-1ra | E-Cadherin |
| HCC-4 | FGF-7 | IL-2 | EpCAM |
| IL-9 | GDF-15 | IL-4 | FAS L |
| IL-17F | GDNF | IL-5 | Fcr RIIB/C |
| IL-18 BPa | GH | IL-6 | Follistatin |
| IL-28A | HB-EGF | IL-6Sr | Galectin-7 |
| IL-29 | HGF | IL-7 | ICAM-2 |
| IL-31 | IGFBP-1 | IL-8 | IL-13 R1 |
| IP-10 | IGFBP-2 | IL-10 | IL-13 R2 |
| I-TAC | IGFBP-3 | IL-11 | IL-17B |
| LIF | IGFBP-4 | IL-12p40 | IL-2 Ra |
| LIGHT | IGFBP-6 | IL-12p70 | IL-2 Rb |
| Lymphotactin | IGF-I | IL-13 | IL-23 |
| MCP-2 | Insulin | IL-15 | LAP |
| MCP-3 | MCSF R | IL-16 | NrCAM |
| MCP-4 | NGF R | IL-17 | PAI-I |
| MDC | NT-3 | MCP-1 | PDGF-AB |
| MIF | NT-4 | MCSF | Resistin |
| MIP-3a | OPG | MIG | SDF-1b |
| MIP-3b | PDGF-AA | MIP-1a | sgp130 |
| MPIF-1 | PlGF | MIP-1b | Shh N |
| MSPa | SCF | MIP-1d | Siglec-5 |
| NAP-2 | SCF R | PDGF-BB | ST2 |
| OPN | TGFa | RANTES | TGF-b2 |
| PARC | TGFb | TIMP-1 | Tie-2 |
| PF4 | TGFb3 | TIMP-2 | TPO |
| SDF-1a | VEGF | TNFa | TRAIL-R4 |
| TARC | VEGF R2 | TNFb | TREM-1 |
| TECK | VEGF R3 | TNF RI | VEGF R1 |
| TSLP | VEGF-D | TNF RII | VEGF-C |

TABLE 2A

Summary of fold changes in the levels of circulating factors in breast cancer patients treated with AC chemotherapy

| | Breast cancer patients treated with AC chemotherapy (N = 16) | | | |
|---|---|---|---|---|
| | Fold change >1.5 | | Fold change <0.5 | |
| Factor | % patients | Average fold bchange | % patients | Average fold change |
| 6Ckine | 6.3 | 5.0 | 18.8 | 0.4 |
| Activin A | 18.8 | 2.3 | 12.5 | 0.4 |
| AgRP | 6.3 | 3.3 | 0.0 | N/A |
| ANG | 6.3 | 1.5 | 0.0 | N/A |
| ANG-1 | 37.5 | 2.7 | 25.0 | 0.4 |
| Angiostatin | 6.3 | 2.0 | 0.0 | N/A |
| AR | 12.5 | 1.9 | 18.8 | 0.4 |
| Axl | 50.0 | 2.7 | 0.0 | N/A |
| BDNF | 37.5 | 2.2 | 6.3 | 0.5 |
| bFGF | 0.0 | N/A | 0.0 | N/A |
| BLC | 75.0 | 4.7 | 0.0 | N/A |
| BMP-4 | 6.3 | 2.1 | 0.0 | N/A |
| BMP-5 | 12.5 | 1.8 | 0.0 | N/A |
| BMP-7 | 12.5 | 2.1 | 0.0 | N/A |
| b-NGF | 6.3 | 1.6 | 18.8 | 0.4 |
| BTC | 12.5 | 11.6 | 0.0 | N/A |
| CathepsinS | 0.0 | N/A | 18.8 | 0.4 |
| CCL28 | 6.3 | 17.8 | 0.0 | N/A |
| CD 40 | 0.0 | N/A | 12.5 | 0.3 |
| Cripto-1 | 6.3 | 1.7 | 0.0 | N/A |
| CTACK | 6.3 | 2.7 | 6.3 | 0.5 |
| CXCL16 | 0.0 | N/A | 0.0 | N/A |
| DAN | 12.5 | 2.0 | 0.0 | N/A |
| DKK-1 | 0.0 | N/A | 12.5 | 0.4 |
| E-Cadherin | 0.0 | N/A | 0.0 | N/A |
| EGF | 18.8 | 3.2 | 31.3 | 0.4 |
| EGF R | 0.0 | N/A | 0.0 | N/A |
| EG-VEGF | 0.0 | N/A | 0.0 | N/A |
| ENA-78 | 37.5 | 3.3 | 0.0 | N/A |
| Eotaxin | 6.3 | 1.7 | 25.0 | 0.4 |

TABLE 2A-continued

Summary of fold changes in the levels of circulating factors in breast cancer patients treated with AC chemotherapy

| | Breast cancer patients treated with AC chemotherapy (N = 16) | | | |
|---|---|---|---|---|
| | Fold change >1.5 | | Fold change <0.5 | |
| Factor | % patients | Average fold bchange | % patients | Average fold change |
| Eotaxin-2 | 0.0 | N/A | 12.5 | 0.3 |
| Eotaxin-3 | 31.3 | 3.1 | 6.3 | 0.1 |
| EpCAM | 25.0 | 1.9 | 6.3 | 0.5 |
| FAS L | 6.3 | 3.0 | 0.0 | N/A |
| Fcr RIIB/C | 31.3 | 2.6 | 0.0 | N/A |
| FGF-4 | 12.5 | 1.8 | 0.0 | N/A |
| FGF-7 | 18.8 | 1.8 | 6.3 | 0.4 |
| Follistatin | 25.0 | 2.3 | 0.0 | N/A |
| Galectin-7 | 25.0 | 2.0 | 6.3 | 0.5 |
| GCP-2 | 37.5 | 2.6 | 12.5 | 0.3 |
| G-CSF | 50.0 | 2.4 | 6.3 | 0.5 |
| GDF-15 | 100.0 | 6.2 | 0.0 | N/A |
| GDNF | 0.0 | N/A | 12.5 | 0.4 |
| GH | 31.3 | 2.1 | 18.8 | 0.2 |
| GM-CSF | 6.3 | 1.5 | 0.0 | N/A |
| GRO | 31.3 | 2.6 | 0.0 | N/A |
| HB-EGF | 6.3 | 1.6 | 0.0 | N/A |
| HCC-1 | 12.5 | 1.6 | 0.0 | N/A |
| HCC-4 | 25.0 | 1.6 | 12.5 | 0.3 |
| HGF | 6.3 | 1.6 | 0.0 | N/A |
| I-309 | 25.0 | 2.4 | 31.3 | 0.4 |
| ICAM-1 | 6.3 | 1.9 | 0.0 | N/A |
| ICAM-2 | 12.5 | 2.0 | 0.0 | N/A |
| IFNg | 0.0 | N/A | 0.0 | N/A |
| IGFBP-1 | 18.8 | 1.9 | 37.5 | 0.3 |
| IGFBP-2 | 12.5 | 1.8 | 0.0 | N/A |
| IGFBP-3 | 6.3 | 4.1 | 0.0 | N/A |
| IGFBP-4 | 0.0 | N/A | 0.0 | N/A |
| IGFBP-6 | 6.3 | 2.2 | 0.0 | N/A |
| IGF-I | 0.0 | N/A | 0.0 | N/A |
| IL-10 | 0.0 | N/A | 0.0 | N/A |
| IL-11 | 31.3 | 2.0 | 0.0 | N/A |
| IL-12p40 | 18.8 | 3.2 | 31.3 | 0.3 |
| IL-12p70 | 18.8 | 2.2 | 6.3 | 0.5 |
| IL-13 | 6.3 | 2.7 | 0.0 | N/A |
| IL-13 R1 | 31.3 | 1.7 | 6.3 | 0.5 |
| IL-13 R2 | 18.8 | 1.9 | 6.3 | 0.5 |
| IL-15 | 6.3 | 2.9 | 0.0 | N/A |
| IL-16 | 25.0 | 2.0 | 6.3 | 0.4 |
| IL-17 | 25.0 | 2.4 | 6.3 | 0.4 |
| IL-17B | 50.0 | 2.1 | 0.0 | N/A |
| IL-17F | 31.3 | 1.7 | 6.3 | 0.3 |
| IL-18 BPa | 18.8 | 5.5 | 12.5 | 0.3 |
| IL-1a | 31.3 | 2.6 | 12.5 | 0.4 |
| IL-1b | 25.0 | 1.9 | 12.5 | 0.5 |
| IL-1ra | 25.0 | 2.6 | 0.0 | N/A |
| IL-2 | 18.8 | 1.6 | 0.0 | N/A |
| IL-2 Ra | 12.5 | 2.7 | 6.3 | 0.4 |
| IL-2 Rb | 18.8 | 1.9 | 6.3 | 0.5 |
| IL-23 | 31.3 | 2.8 | 12.5 | 0.5 |
| IL-28A | 37.5 | 3.6 | 6.3 | 0.4 |
| IL-29 | 6.3 | 5.1 | 0.0 | N/A |
| IL-31 | 12.5 | 2.0 | 0.0 | N/A |
| IL-4 | 12.5 | 1.8 | 0.0 | N/A |
| IL-5 | 6.3 | 15.2 | 0.0 | N/A |
| IL-6 | 6.3 | 1.9 | 0.0 | N/A |
| IL-6sR | 6.3 | 1.6 | 0.0 | N/A |
| IL-7 | 12.5 | 2.3 | 0.0 | N/A |
| IL-8 | 18.8 | 1.7 | 0.0 | N/A |
| IL-9 | 6.3 | 11.2 | 0.0 | N/A |
| Insulin | 25.0 | 1.8 | 0.0 | N/A |
| IP-10 | 25.0 | 3.5 | 12.5 | 0.3 |
| I-TAC | 18.8 | 3.9 | 37.5 | 0.3 |
| LAP | 31.3 | 1.9 | 6.3 | 0.5 |
| LIF | 12.5 | 4.9 | 12.5 | 0.2 |
| LIGHT | 6.3 | 3.5 | 6.3 | 0.5 |
| Lymphotactin | 25.0 | 2.4 | 6.3 | 0.4 |
| MCP-1 | 0.0 | N/A | 12.5 | 0.4 |
| MCP-2 | 18.8 | 1.7 | 6.3 | 0.4 |
| MCP-3 | 31.3 | 2.4 | 0.0 | N/A |
| MCP-4 | 6.3 | 9.7 | 12.5 | 0.4 |
| MCSF | 43.8 | 24.5 | 18.8 | 0.3 |
| MCSF R | 0.0 | N/A | 0.0 | N/A |
| MDC | 12.5 | 3.9 | 37.5 | 0.3 |
| MIF | 43.8 | 3.3 | 18.8 | 0.3 |
| MIG | 31.3 | 3.0 | 18.8 | 0.5 |
| MIP-1a | 12.5 | 1.9 | 12.5 | 0.4 |
| MIP-1b | 0.0 | N/A | 0.0 | N/A |
| MIP-1d | 37.5 | 2.1 | 12.5 | 0.4 |
| MIP-3a | 18.8 | 7.8 | 25.0 | 0.4 |
| MIP-3b | 0.0 | N/A | 62.5 | 0.4 |
| MPIF-1 | 56.3 | 2.4 | 0.0 | N/A |
| MSPa | 12.5 | 2.1 | 12.5 | 0.2 |
| NAP-2 | 0.0 | N/A | 0.0 | N/A |
| NGFR | 12.5 | 2.0 | 0.0 | N/A |
| NrCAM | 18.8 | 2.1 | 0.0 | N/A |
| NT-3 | 18.8 | 1.5 | 6.3 | 0.4 |
| NT-4 | 25.0 | 1.9 | 6.3 | 0.0 |
| OPG | 6.3 | 1.9 | 0.0 | N/A |
| OPN | 12.5 | 3.7 | 12.5 | 0.3 |
| PAI-I | 6.3 | 1.8 | 6.3 | 0.5 |
| PARC | 18.8 | 1.6 | 0.0 | N/A |
| PDGF-AA | 50.0 | 3.2 | 18.8 | 0.3 |
| PDGF-AB | 37.5 | 2.8 | 6.3 | 0.4 |
| PDGF-BB | 37.5 | 3.6 | 12.5 | 0.3 |
| PF4 | 18.8 | 1.6 | 0.0 | N/A |
| PIGF | 12.5 | 2.2 | 12.5 | 0.4 |
| RANTES | 31.3 | 2.6 | 6.3 | 0.3 |
| Resistin | 18.8 | 1.8 | 6.3 | 0.4 |
| SCF | 12.5 | 2.1 | 12.5 | 0.4 |
| SCF R | 0.0 | N/A | 0.0 | N/A |
| SDF-1a | 0.0 | N/A | 6.3 | 0.5 |
| SDF-1b | 6.3 | 2.1 | 12.5 | 0.3 |
| sgp130 | 6.3 | 1.5 | 6.3 | 0.2 |
| Shh N | 6.3 | 2.2 | 0.0 | N/A |
| Siglec-5 | 12.5 | 1.5 | 0.0 | N/A |
| ST2 | 68.8 | 2.5 | 0.0 | N/A |
| TARC | 25.0 | 2.0 | 0.0 | N/A |
| TECK | 12.5 | 3.1 | 0.0 | N/A |
| TGFa | 18.8 | 2.1 | 12.5 | 0.5 |
| TGFb | 31.3 | 1.6 | 0.0 | N/A |
| TGF-b2 | 6.3 | 1.8 | 6.3 | 0.5 |
| TGFb3 | 18.8 | 2.0 | 6.3 | 0.1 |
| Tie-2 | 31.3 | 1.7 | 6.3 | 0.4 |
| TIMP-1 | 12.5 | 2.2 | 0.0 | N/A |
| TIMP-2 | 6.3 | 1.9 | 0.0 | N/A |
| TNF RI | 0.0 | N/A | 0.0 | N/A |
| TNF RII | 0.0 | N/A | 0.0 | N/A |
| TNFa | 12.5 | 1.7 | 0.0 | N/A |
| TNFb | 12.5 | 1.7 | 0.0 | N/A |
| TPO | 12.5 | 2.1 | 0.0 | N/A |
| TRAIL-R4 | 12.5 | 2.3 | 0.0 | N/A |
| TREM-1 | 18.8 | 1.7 | 0.0 | N/A |
| TSLP | 43.8 | 1.8 | 6.3 | 0.4 |
| VEGF A | 18.8 | 1.9 | 12.5 | 0.1 |
| VEGF R1 | 25.0 | 2.1 | 0.0 | N/A |
| VEGF R2 | 31.3 | 1.9 | 6.3 | 0.5 |
| VEGF R3 | 0.0 | N/A | 12.5 | 0.4 |
| VEGF-C | 6.3 | 1.5 | 0.0 | N/A |
| VEGF-D | 25.0 | 2.4 | 12.5 | 0.3 |

TABLE 2B

Summary of fold changes in the levels of circulating factors in colorectal cancer patients treated with FOLFOX ™ chemotherapy Colorectal cancer patients treated with FOLFOX ™ chemotherapy (N = 19)

| Factor | Fold change >1.5 % patients | Fold change >1.5 Average fold change | Fold change <0.5 % patients | Fold change <0.5 Average fold change |
|---|---|---|---|---|
| 6Ckine | 5.3 | 1.6 | 42.1 | 0.4 |
| Activin A | 21.1 | 1.8 | 10.5 | 0.5 |
| AgRP | 10.5 | 1.6 | 5.3 | 0.4 |
| ANG | 26.3 | 2.2 | 5.3 | 0.4 |
| ANG-1 | 0.0 | N/A | 10.5 | 0.4 |
| Angiostatin | 5.3 | 2.9 | 0.0 | N/A |
| AR | 5.3 | 2.1 | 10.5 | 0.3 |
| Axl | 21.1 | 1.7 | 0.0 | N/A |
| BDNF | 21.1 | 1.7 | 36.8 | 0.4 |
| bFGF | 5.3 | 1.7 | 21.1 | 0.4 |
| BLC | 57.9 | 3.5 | 10.5 | 0.5 |
| BMP-4 | 10.5 | 2.2 | 31.6 | 0.3 |
| BMP-5 | 10.5 | 1.7 | 10.5 | 0.3 |
| BMP-7 | 5.3 | 1.6 | 5.3 | 0.4 |
| b-NGF | 5.3 | 2.0 | 26.3 | 0.3 |
| BTC | 0.0 | N/A | 10.5 | 0.4 |
| CathepsinS | 5.3 | 3.0 | 0.0 | N/A |
| CCL28 | 0.0 | N/A | 10.5 | 0.2 |
| CD 40 | 0.0 | N/A | 15.8 | 0.4 |
| Cripto-1 | 5.3 | 1.8 | 0.0 | N/A |
| CTACK | 0.0 | N/A | 5.3 | 0.3 |
| CXCL16 | 0.0 | N/A | 5.3 | 0.2 |
| DAN | 15.8 | 2.1 | 5.3 | 0.2 |
| DKK-1 | 0.0 | N/A | 0.0 | N/A |
| E-Cadherin | 5.3 | 1.6 | 5.3 | 0.5 |
| EGF | 10.5 | 1.8 | 15.8 | 0.3 |
| EGF R | 5.3 | 1.6 | 5.3 | 0.5 |
| EG-VEGF | 5.3 | 1.6 | 5.3 | 0.4 |
| ENA-78 | 0.0 | N/A | 31.6 | 0.4 |
| Eotaxin | 10.5 | 1.5 | 10.5 | 0.3 |
| Eotaxin-2 | 0.0 | N/A | 21.1 | 0.4 |
| Eotaxin-3 | 0.0 | N/A | 10.5 | 0.4 |
| EpCAM | 10.5 | 1.5 | 5.3 | 0.3 |
| FAS L | 5.3 | 1.6 | 5.3 | 0.5 |
| Fcr RIIB/C | 31.6 | 2.4 | 0.0 | N/A |
| FGF-4 | 5.3 | 1.5 | 5.3 | 0.2 |
| FGF-7 | 15.8 | 2.1 | 10.5 | 0.2 |
| Follistatin | 10.5 | 2.1 | 5.3 | 0.4 |
| Galectin-7 | 0.0 | N/A | 21.1 | 0.4 |
| GCP-2 | 0.0 | N/A | 10.5 | 0.4 |
| G-CSF | 36.8 | 3.6 | 21.1 | 0.4 |
| GDF-15 | 78.9 | 2.9 | 0.0 | N/A |
| GDNF | 10.5 | 2.8 | 5.3 | 0.2 |
| GH | 21.1 | 3.3 | 21.1 | 0.3 |
| GM-CSF | 0.0 | N/A | 15.8 | 0.3 |
| GRO | 31.6 | 2.0 | 0.0 | N/A |
| HB-EGF | 5.3 | 1.5 | 31.6 | 0.2 |
| HCC-1 | 5.3 | 1.6 | 10.5 | 0.4 |
| HCC-4 | 5.3 | 4.3 | 5.3 | 0.5 |
| HGF | 15.8 | 3.8 | 15.8 | 0.5 |
| I-309 | 10.5 | 1.7 | 36.8 | 0.3 |
| ICAM-1 | 0.0 | N/A | 10.5 | 0.4 |
| ICAM-2 | 5.3 | 3.4 | 10.5 | 0.4 |
| IFNg | 5.3 | 1.6 | 15.8 | 0.4 |
| IGFBP-1 | 5.3 | 3.5 | 36.8 | 0.4 |
| IGFBP-2 | 0.0 | N/A | 15.8 | 0.4 |
| IGFBP-3 | 10.5 | 3.1 | 15.8 | 0.4 |
| IGFBP-4 | 15.8 | 2.3 | 15.8 | 0.4 |
| IGFBP-6 | 0.0 | N/A | 26.3 | 0.4 |
| IGF-I | 10.5 | 6.2 | 0.0 | N/A |
| IL-10 | 5.3 | 1.7 | 15.8 | 0.4 |
| IL-11 | 5.3 | 2.1 | 21.1 | 0.4 |
| IL-12p40 | 0.0 | N/A | 31.6 | 0.3 |
| IL-12p70 | 5.3 | 2.9 | 10.5 | 0.3 |
| IL-13 | 0.0 | N/A | 5.3 | 0.3 |
| IL-13 R1 | 10.5 | 2.5 | 5.3 | 0.5 |
| IL-13 R2 | 0.0 | N/A | 10.5 | 0.5 |
| IL-15 | 0.0 | N/A | 10.5 | 0.4 |
| IL-16 | 0.0 | N/A | 10.5 | 0.3 |
| IL-17 | 15.8 | 6.1 | 10.5 | 0.4 |
| IL-17B | 5.3 | 1.6 | 10.5 | 0.4 |
| IL-17F | 0.0 | N/A | 5.3 | 0.5 |
| IL-18 BPa | 5.3 | 3.1 | 5.3 | 0.5 |
| IL-1a | 15.8 | 2.1 | 15.8 | 0.4 |
| IL-1b | 5.3 | 1.5 | 26.3 | 0.2 |
| IL-1ra | 5.3 | 2.1 | 15.8 | 0.4 |
| IL-2 | 0.0 | N/A | 5.3 | 0.4 |
| IL-2 Ra | 10.5 | 2.6 | 15.8 | 0.4 |
| IL-2 Rb | 5.3 | 2.6 | 21.1 | 0.4 |
| IL-23 | 10.5 | 5.1 | 5.3 | 0.4 |
| IL-28A | 10.5 | 2.0 | 10.5 | 0.4 |
| IL-29 | 0.0 | N/A | 5.3 | 0.3 |
| IL-31 | 5.3 | 1.6 | 5.3 | 0.5 |
| IL-4 | 5.3 | 4.9 | 15.8 | 0.3 |
| IL-5 | 0.0 | N/A | 15.8 | 0.3 |
| IL-6 | 0.0 | N/A | 5.3 | 0.5 |
| IL-6sR | 5.3 | 1.8 | 5.3 | 0.4 |
| IL-7 | 0.0 | N/A | 15.8 | 0.4 |
| IL-8 | 0.0 | N/A | 15.8 | 0.4 |
| IL-9 | 5.3 | 10.5 | 0.0 | N/A |
| Insulin | 15.8 | 14.4 | 21.1 | 0.3 |
| IP-10 | 10.5 | 2.3 | 42.1 | 0.4 |
| I-TAC | 5.3 | 2.8 | 31.6 | 0.4 |
| LAP | 10.5 | 2.7 | 10.5 | 0.4 |
| LIF | 15.8 | 2.3 | 21.1 | 0.4 |
| LIGHT | 5.3 | 2.0 | 5.3 | 0.3 |
| Lymphotactin | 5.3 | 1.7 | 5.3 | 0.4 |
| MCP-1 | 15.8 | 1.9 | 21.1 | 0.4 |
| MCP-2 | 5.3 | 1.7 | 5.3 | 0.4 |
| MCP-3 | 5.3 | 1.6 | 21.1 | 0.4 |
| MCP-4 | 0.0 | N/A | 10.5 | 0.3 |
| MCSF | 21.1 | 4.0 | 26.3 | 0.4 |
| MCSF R | 10.5 | 1.7 | 10.5 | 0.4 |
| MDC | 0.0 | N/A | 10.5 | 0.3 |
| MIF | 5.3 | 7.5 | 21.1 | 0.3 |
| MIG | 15.8 | 1.7 | 26.3 | 0.3 |
| MIP-1a | 0.0 | N/A | 26.3 | 0.3 |
| MIP-1b | 5.3 | 1.6 | 15.8 | 0.3 |
| MIP-1d | 31.6 | 2.0 | 0.0 | N/A |
| MIP-3a | 21.1 | 2.1 | 10.5 | 0.4 |
| MIP-3b | 26.3 | 2.7 | 52.6 | 0.3 |
| MPIF-1 | 0.0 | N/A | 26.3 | 0.3 |
| MSPa | 15.8 | 1.9 | 15.8 | 0.3 |
| NAP-2 | 5.3 | 4.3 | 10.5 | 0.2 |
| NGF R | 21.1 | 2.3 | 10.5 | 0.3 |
| NrCAM | 10.5 | 3.6 | 15.8 | 0.5 |
| NT-3 | 5.3 | 9.9 | 15.8 | 0.4 |
| NT-4 | 10.5 | 1.9 | 31.6 | 0.3 |
| OPG | 10.5 | 4.1 | 10.5 | 0.3 |
| OPN | 15.8 | 2.7 | 15.8 | 0.3 |
| PAI-I | 21.1 | 2.4 | 5.3 | 0.4 |
| PARC | 5.3 | 2.0 | 15.8 | 0.3 |
| PDGF-AA | 10.5 | 2.0 | 47.4 | 0.3 |
| PDGF-AB | 5.3 | 2.8 | 10.5 | 0.4 |
| PDGF-BB | 10.5 | 2.3 | 26.3 | 0.4 |
| PF4 | 0.0 | N/A | 15.8 | 0.4 |
| PIGF | 10.5 | 2.2 | 21.1 | 0.3 |
| RANTES | 10.5 | 1.9 | 15.8 | 0.4 |
| Resistin | 36.8 | 2.0 | 0.0 | N/A |
| SCF | 26.3 | 1.6 | 10.5 | 0.3 |
| SCF R | 5.3 | 4.1 | 15.8 | 0.4 |
| SDF-1a | 5.3 | 1.6 | 57.9 | 0.3 |
| SDF-1b | 15.8 | 3.1 | 0.0 | N/A |
| sgp130 | 15.8 | 2.3 | 0.0 | N/A |
| Shh N | 10.5 | 3.2 | 10.5 | 0.4 |
| Siglec-5 | 15.8 | 2.7 | 5.3 | 0.5 |
| ST2 | 36.8 | 9.6 | 5.3 | 0.4 |
| TARC | 26.3 | 4.7 | 10.5 | 0.3 |

TABLE 2B-continued

Summary of fold changes in the levels of circulating factors in colorectal cancer patients treated with FOLFOX™ chemotherapy

| | Colorectal cancer patients treated with FOLFOX™ chemotherapy (N = 19) | | | |
|---|---|---|---|---|
| | Fold change >1.5 | | Fold change <0.5 | |
| Factor | % patients | Average fold change | % patients | Average fold change |
| TECK | 0.0 | N/A | 21.1 | 0.3 |
| TGFa | 5.3 | 1.8 | 31.6 | 0.3 |
| TGFb | 5.3 | 2.3 | 15.8 | 0.3 |
| TGF-b2 | 10.5 | 3.4 | 5.3 | 0.4 |
| TGFb3 | 15.8 | 62.0 | 31.6 | 0.1 |
| Tie-2 | 10.5 | 3.3 | 5.3 | 0.5 |
| TIMP-1 | 0.0 | N/A | 5.3 | 0.3 |
| TIMP-2 | 0.0 | N/A | 5.3 | 0.5 |
| TNF RI | 21.1 | 1.7 | 10.5 | 0.3 |
| TNF RII | 5.3 | 1.5 | 10.5 | 0.2 |
| TNFa | 10.5 | 139.0 | 21.1 | 0.4 |
| TNFb | 5.3 | 1.6 | 15.8 | 0.4 |
| TPO | 15.8 | 3.0 | 10.5 | 0.5 |
| TRAIL-R4 | 21.1 | 2.4 | 10.5 | 0.4 |
| TREM-1 | 15.8 | 4.3 | 0.0 | N/A |
| TSLP | 5.3 | 2.0 | 31.6 | 0.3 |
| VEGF A | 10.5 | 3.8 | 42.1 | 0.2 |
| VEGF R1 | 5.3 | 4.3 | 21.1 | 0.4 |
| VEGF R2 | 5.3 | 3.5 | 15.8 | 0.4 |
| VEGF R3 | 15.8 | 2.3 | 21.1 | 0.3 |
| VEGF-C | 10.5 | 2.2 | 5.3 | 0.4 |
| VEGF-D | 10.5 | 2.6 | 21.1 | 0.2 |

TABLE 3

Profile of circulating factors indicating a host response to chemotherapy in human subjects 6Ckine (CCL21)
Activin A
ANG (Angiogenin)
ANG-1 (Angiopoeitin-1)
Amphiregulin (AR)
Axl
BDNF
bFGF
BLC (CXCL13)
BMP-4
b-NGF
CathepsinS
EGF
ENA-78 (CXCL5)
Eotaxin (CCL11)
Eotaxin-2 (CCL24)
Eotaxin-3 (CCL26)
EpCAM
Fcr RIIB/C
FGF-7
Follistatin
Galectin-7
GCP-2
G-CSF
GDF-15
GH
GRO
HB-EGF
HCC-4 (CCL16)
I-309 (CCL1)
IGFBP-1
IGFBP-6
IL-11
IL-12p40
IL-12p70
IL-13 R1
IL-13 R2
IL-16
IL-17
IL-17B
IL-17F
IL-18 BPa
IL-1α
IL-1β
IL-1ra
IL-2
IL-2 Rb
IL-23
IL-28A
IL-8
IP-10 (CXCL10)
I-TAC (CXCL11)
LAP
LIF
Lymphotactin
MCP-1 (CCL2)
MCP-2 (CCL8)
MCP-3 (CCL7)
MCSF
MDC (CCL22)
MIF
MIG (CXCL9)
MIP-1α (CCL3)
MIP-1δ (CCL15)
MIP-3α (CCL20)
MIP-3β (CCL19)
MPIF-1
NGF R
NrCAM
NT-3
NT-4
PAI-I
PARC
PDGF-AA
PDGF-AB
PDGF-BB
PF4 (CXCL4)
PIGF
RANTES (CCL5)
Resistin
SCF
SDF-1α (CXCL12)
ST2 (IL-1R4)
TARC (CCL17)
TECK
TGFα
TGFβ
TGFβ3
Tie-2
TNF RI
TNFα
TRAIL-R4
TREM-1
TSLP
VEGF
VEGF R1
VEGF R2
VEGF R3
VEGF-D

TABLE 4

List of 308 factors participating in the antibody array screen performed with plasma from mice receiving chemotherapy or bortezomib
Mouse L308 Array ™ (RayBiotech; Cat no: AAM-BLG-1-2)

6Ckine, Activin A, Activin C, Activin RIB/ALK-4, Adiponectin/Acrp30, AgRP, ALCAM, Angiopoietin-like 2, Angiopoietin-like 3, AREG (Amphiregulin), Artemin, Axl, bFGF, B7-1/CD80, BAFF R/TNFRSF13C, BCMA/TNFRSF17, beta-Catenin, BLC, BTC (Betacellulin), Cardiotrophin-1, CCL1/I-309/TCA-3, CCL28, CCL4/MIP-1 beta, CCL7/MCP-3/MARC, CCL8/MCP-2, CCR10, CCR3, CCR4, CCR6, CCR7, CCR9, CD11b, CD14, CRP, CD27/TNFRSF7, CD27 Ligand/TNFSF7, CD30, CD30 L, CD40, CD40 Ligand/TNFSF5, Cerberus 1, Chordin-Like 2, Coagulation Factor III/Tissue Factor, Common gamma Chain/IL-2 R gamma, CRG-2, Cripto, Crossveinless-2, Cryptic, Csk, CTACK, CTLA-4/CD152, CXCL14/BRAK, CXCL16, CXCR2/IL-8 RB, CXCR3, CXCR4, CXCR6, DAN, Decorin, DKK-1, Dkk-3, Dkk-4, DPPIV/CD26, DR3/TNFRSF25, Dtk, EDAR, EGF R, EG-VEGF/PK1, Endocan, Endoglin/CD105, Endostatin, Eotaxin, Eotaxin-2, Epigen, Epiregulin, Erythropoietin (EPO), E-Selectin, FADD, FAM3B, Fas/TNFRSF6, Fas Ligand, FCrRIIB/CD32b, FGF R3, FGF R4, FGF R5 beta, FGF-21, Flt-3 Ligand, FLRG (Follistatin), Follistatin-like 1, Fractalkine, Frizzled-1, Frizzled-6, Frizzled-7, Galectin-3, G-CSF, GDF-1, GDF-3, GDF-5, GDF-8, GDF-9, GFR alpha-2/GDNF R alpha-2, GFR alpha-3/GDNF R alpha-3, GFR alpha-4/GDNF R alpha-4, GITR, GITR Ligand/TNFSF18, Glut2, GM-CSF, Granzyme B, Granzyme D, Granzyme G, Gremlin, Growth Hormone R, HGF R, HGF, HVEM/TNFRSF14, ICAM-1, ICAM-2/CD102, ICAM-5, ICK, IFN-alpha/beta R1, IFN-alpha/beta R2, IFN-beta, IFN-gamma, IFN-gamma R1, IGFBP-1, IGFBP-2, IGFBP-3, IGFBP-5, IGFBP-6, IGFBP-rp1/IGFBP-7, IGF-I, IGF-II, IL-1 alpha, IL-1 beta, IL-1 R4/ST2, IL-1 R6/IL-1 R rp2, IL-1 R9, IL-1 RI, IL-1 RII, IL-2, IL-2 R alpha, IL-2 R beta, IL-3, IL-3 R alpha, IL-3 R beta, IL-4, IL-4 R, IL-5, IL-5 R alpha, IL-6, IL-6 R, IL-7, IL-7 R alpha, IL-9, IL-9 R, IL-10, IL-10 R alpha, IL-11, IL-12 p40/p70, IL-12 p70, IL-12 R beta 1, IL-13, IL-13 R alpha 2, IL-15, IL-15 R alpha, IL-16, IL-17, IL-17B R, IL-17C, IL-17D, IL-17E, IL-17F, IL-17R, IL-17RC, IL-17RD, IL-18 R alpha/IL-1 R5, IL-20, IL-20 R alpha, IL-21, IL-21 R, IL-22, IL-22BP, IL-23, IL-23 R, IL-24, IL-27, IL-28/IFN-lambda, IL-31, IL-31 RA, Insulin, Integrin beta 2/CD18, I-TAC, KC, Kremen-1, Kremen-2, Lefty-1, Leptin R, LEPTIN(OB), LIF, LIGHT/TNFSF14, LIX, LRP-6, L-Selectin, Lungkine, Lymphotactin, Lymphotoxin beta R/TNFRSF3, MAdCAM-1, MCP-1, MCP-5, M-CSF, MDC, MFG-E8, MFRP, MIG, MIP-1 alpha, MIP-1 gamma, MIP-2, MIP-3 alpha, MIP-3 beta, MMP-2, MMP-3, MMP-9, MMP-12, MMP-14/LEM-2, MMP-24/MT5-MMP, Neuregulin-3/NRG3, Neurturin, NGF R/TNFRSF16, NOV/CCN3, Osteoactivin/GPNMB, Osteopontin, Osteoprotegerin, OX40 Ligand/TNFSF4, PDGF C, PDGF R alpha, PDGF R beta, Pentraxin3/TSG-14, PF-4, PlGF-2, Progranulin, Prolactin, P-Selectin, RAGE, RANTES, RELM beta, Resistin, S100A10, SCF, SCF R/c-kit, SDF-1, Serum Amyloid A1, Shh-N, SIGIRR, SLPI, Soggy-1, SPARC, Spinesin Ectodomain, TACI/TNFRSF13B, TARC, TCA-3, TCCR/WSX-1, TECK, TFPI, TGF-beta 1, TGF-beta 2, TGF-beta 3, TGF-beta RI/ALK-5, TGF-beta RII, Thrombospondin, Thymus Chemokine-1, Tie-2, TIMP-1, TIMP-2, TIMP-4, TL1A/TNFSF15, TLR1, TLR2, TLR3, TLR4, TMEFF1/Tomoregulin-1, TNF RI/TNFRSF1A, TNF RII, TNF-alpha, TNF-beta/TNFSF1B, TPO, TRAIL/TNFSF10, TRAIL R2/TNFRSF10B, TRANCE/TNFSF11, TREM-1, TROY, TSLP, TSLP R, TWEAK/TNFSF12, TWEAK R/TNFRSF12, Ubiquitin, uPAR, Urokinase, VCAM-1, VE-Cadherin, VEGF, VEGF R1, VEGF R2, VEGF R3, VEGF-B, VEGF-C, VEGF-D, WIF-1, WISP-1/CCN4

TABLE 5

Summary of fold changes in the levels of circulating factors in chemotherapy-treated vs control BALB/c mice

| | Fold change (chemotherapy-treated vs control) | |
|---|---|---|
| | Paclitaxel ™ | FOLFOX ™ |
| Cardiotrophin-1 | >10 | NC |
| CRP | >10 | NC |
| CRG-2 | >10 | NC |
| Cripto | >10 | 0.2 |
| CTACK | NC | 0.5 |
| CXCL14/BRAK | 2.6 | 3.5 |
| CXCL16 | 4.4 | 0.3 |
| CXCR2/IL-8 RB | 2.0 | NC |
| CXCR6 | 3.6 | NC |
| Dkk-3 | >10 | NC |
| Endocan | 4.4 | NC |
| Endostatin | 4.9 | NC |
| Eotaxin-2 | 3.4 | >10 |
| Erythropoietin (EPO) | 3.9 | NC |
| FCrRIIB/CD32b | NC | 0.2 |
| Frizzled-6 | 2.2 | NC |
| Frizzled-7 | 6.1 | NC |
| GDF-5 | NC | >10 |
| GFR alpha-4/GDNF R alpha-4 | NC | 0.2 |
| GITR | >10 | NC |
| GM-CSF | 2.4 | NC |
| HVEM/TNFRSF14 | NC | >10 |
| IGFBP-1 | >10 | NC |
| IL-1 alpha | >10 | NC |
| IL-1 R4/ST2 | 1.9 | >10 |
| IL-3 R alpha | >10 | NC |
| IL-7 R alpha | 8.8 | NC |
| IL-9 R | 5.7 | NC |
| IL-10 | NC | >10 |
| IL-11 | NC | >10 |
| IL-12 p70 | >10 | 1.5 |
| IL-15 | 2.5 | >10 |
| IL-15 R alpha | 3.4 | >10 |
| IL-17 | NC | >10 |

TABLE 5-continued

Summary of fold changes in the levels of circulating factors in chemotherapy-treated vs control BALB/c mice

| | Fold change (chemotherapy-treated vs control) | |
|---|---|---|
| | Paclitaxel ™ | FOLFOX ™ |
| IL-17R | 2.6 | NC |
| IL-18 R alpha/IL-1 R5 | >10 | NC |
| IL-20 | >10 | NC |
| IL-23 R | 1.8 | NC |
| IL-27 | 2.0 | NC |
| IL-28/IFN-lambda | 5.4 | >10 |
| IL-31 | >10 | NC |
| LIF | >10 | NC |
| LIX | >10 | NC |
| LRP-6 | >10 | NC |
| Lungkine | 2.0 | NC |
| Lymphotoxin beta R/TNFRSF3 | 1.6 | NC |
| MAdCAM-1 | >10 | NC |
| MCP-1 | >10 | NC |
| M-CSF | 1.8 | NC |
| MIP-1 gamma | >10 | NC |
| MIP-2 | 3.1 | >10 |
| MMP-9 | 4.3 | NC |
| PF-4 | 3.6 | NC |
| Prolactin | 4.1 | NC |
| P-Selectin | >10 | NC |
| SDF-1 | >10 | NC |
| SLPI | NC | >10 |
| Soggy-1 | 3.6 | >10 |
| TACI/TNFRSF13B | >10 | NC |
| TARC | >10 | NC |
| TCA-3 | 3.0 | >10 |
| TGF-beta 1 | NC | >10 |
| TGF-beta 2 | 3.4 | NC |
| TGF-beta RII | 2.2 | NC |
| Thrombospondin | >10 | >10 |
| Thymus Chemokine-1 | >10 | NC |
| TNF-alpha | 2.8 | NC |
| TNF-beta/TNFSF1B | 2.9 | >10 |
| TRAIL/TNFSF10 | NC | >10 |
| TPO | >10 | NC |
| TWEAK R/TNFRSF12 | >10 | NC |
| VEGFC | >10 | NC |
| WISP-1/CCN4 | 3.7 | >10 |

NC, no change

TABLE 6

Summary of fold changes in the levels of circulating factors in bortezomib-treated vs control BALB/c mice

| | Fold change (bortezomib-treated vs control) |
|---|---|
| CCL28 | 3.9 |
| CCR9 | 1.9 |
| CD11b | 2.6 |
| CRP | 3.1 |
| CD27/TNFRSF7 | 1.5 |
| CTACK | 2.0 |
| Dtk | 6.6 |
| EG-VEGF/PK1 | 1.5 |
| Fas/TNFRSF6 | 2.2 |
| FCrRIIB/CD32b | 5.5 |
| FGF R5 beta | 3.0 |
| Follistatin-like 1 | >10 |
| Frizzled-6 | 5.9 |
| GDF-8 | 2.3 |
| GFR alpha-4/GDNF R alpha-4 | 6.4 |
| Glut2 | 1.9 |
| HVEM/TNFRSF14 | 2.3 |
| ICAM-1 | 3.3 |
| IFN-beta | 6.9 |
| IFN-gamma | 2.1 |
| IFN-gamma R1 | 1.4 |
| IGFBP-1 | 2.2 |
| IGFBP-3 | 3.6 |
| IL-1 alpha | 2.5 |
| IL-1 R4/ST2 | 1.8 |
| IL-1 RI | 3.5 |
| IL-3 | 2.5 |
| IL-5 | 4.1 |
| IL-6 | 4.6 |
| IL-6 R | >10 |
| IL-10 | >10 |
| IL-11 | 3.1 |
| IL-12 p70 | 1.6 |
| IL-12 R beta 1 | >10 |
| IL-13 | >10 |
| IL-17BR | >10 |
| IL-17C | >10 |
| IL-17E | >10 |
| IL-31 | >10 |
| IL-31 RA | >10 |
| Lungkine | 4.9 |
| Lymphotoxin beta R/TNFRSF3 | 1.9 |
| MCP-1 | 2.6 |
| M-CSF | >10 |
| MIP-3 beta | >10 |
| Neuregulin-3/NRG3 | >10 |
| Osteoporotegerin | >10 |
| PlGF-2 | 10.0 |
| RAGE | >10 |
| TECK | >10 |
| TGF-beta 3 | >10 |
| Thymus Chemokine-1 | >10 |
| TL1A/TNFSF15 | >10 |
| TLR4 | >10 |
| TPO | >10 |
| TRANCE/TNFSF11 | 3.7 |
| TROY | >10 |
| VEGF-D | >10 |

TABLE 7

List of 53 factors participating in the antibody array screen performed with plasma from irradiated or post-surgery mice
Proteome Profiler Mouse Angiogenesis Array kit ™
(R&D Systems; Cat no: ARY015)

ADAMTS1/METH1
AR
ANG
Ang-1
Ang-3
Coagulation Factor III/TF
CXCL16
Cyr61/CCN1
DLL4
DPPIV/CD26
EGF
Endoglin/CD105
Endostatin
ET-1
FGF-1
FGF-2
FGF-7
Fractalkine/CX3CL1
GM-CSF
HB-EGF
HGF
IGFBP-1

TABLE 7-continued

List of 53 factors participating in the antibody
array screen performed with plasma
from irradiated or post-surgery mice
Proteome Profiler Mouse Angiogenesis Array kit ™
(R&D Systems; Cat no: ARY015)

IGFBP-2
IGFBP-3
IL-1alfa
IL1 beta
IL-10
IP-10/CXCL10
KC/CXCL1
Leptin
MCP-1
MIP-1α/CCL3
MMP-3
MMP-8
MMP-9
NOV/CCN3
OPN
PD-ECGF
PDGF-AA
PDGF-BB
Pentraxin-3/TSG-14
Platelet Factor 4/CXCL4
PLGF-2
PRE
Proliferin
SDF-1
PAI-1
PEDF
TSP-2
TIMP-1
TIMP-4
VEGF
VEGF-B

TABLE 8A

Summary of fold changes in the levels of circulating
factors in 2Gy-irradiated vs control BALB/c mice

|  | Fold change (Irradiated vs control) |
| --- | --- |
| ANG | 2.5 |
| Ang-1 | 4.3 |
| Cyr61/CCN1 | 4.1 |
| DPPIV/CD26 | 2.1 |
| EGF | 2.6 |
| Endoglin/CD105 | 4.0 |
| FGF-1 | 3.8 |
| IL-10 | 2.1 |
| Leptin | 3.2 |
| MCP-1 | 2.9 |
| MMP-3 | 3.0 |
| PDGF-AA | 2.9 |
| PDGF-BB | 4.2 |
| Pentraxin-3/TSG-14 | 3.0 |
| PLGF-2 | 3.0 |
| SDF-1 | 5.5 |
| TIMP-1 | 4.3 |

TABLE 8B

Summary of fold changes in the levels of circulating
factors in 2Gy irradiated vs control BALB/c mice

|  | Fold change (Irradiated vs control) |
| --- | --- |
| VEGF R1 | 2.6 |
| TWEAK | 2.6 |

TABLE 8B-continued

Summary of fold changes in the levels of circulating
factors in 2Gy irradiated vs control BALB/c mice

|  | Fold change (Irradiated vs control) |
| --- | --- |
| TremL1 | 2.2 |
| TARC | 1.9 |
| RANTES | 1.6 |
| MIP-1a | 2.2 |
| MIG | 1.9 |
| MCSF | 3.0 |
| MCP-5 | 4.1 |
| LIX | 2.9 |
| KC | 1.8 |
| IL-9 | 15.9 |
| IL-7 | 6.0 |
| IL-6 | 3.0 |
| IL-4 | 2.9 |
| IL-22 | 2.9 |
| IL-21 | 2.9 |
| IL-1a | 3.1 |
| IL-17B R | 1.9 |
| IL-17B | 2.2 |
| IL-15 | 3.0 |
| IL-13 | 4.3 |
| GM-CSF | 1.7 |
| G-CSF | 2.2 |
| Galectin-7 | 2.3 |
| Galectin-3 | 1.7 |
| Fas L | 4.3 |
| Fas | 2.1 |
| Eotaxin-2 | 2.4 |
| CD36 | 2.7 |
| CD30L | 4.1 |
| CD27 | 6.5 |

TABLE 9

Summary of fold changes in the levels of circulating
factors in post-surgery vs control BALB/c mice

|  | Fold change (surgery vs control) |
| --- | --- |
| Ang-1 | 5.9 |
| TF | 0.1 |
| FGF-1 | 6.6 |
| CX3CL1 | 2.3 |
| MCP-1 | 0.5 |
| PD-ECGF | 0.2 |
| PDGF-AA | 3.5 |
| PDGF-BB | 4.0 |
| PLGF-2 | 1.9 |
| PRL | 7.5 |
| TSP-2 | 0.2 |
| TIMP-1 | 0.2 |

TABLE 10

List of 111 factors participating in the antibody array screen
performed with plasma from mice receiving anti-PD-1 therapy
Proteome Profiler Mouse XL Cytokine Array ™
(R&D Systems; Cat no: ARY028)

Adiponectin/Acrp30
Amphiregulin
Angiopoietin-1
Angiopoietin-2
Angiopoietin-like 3
BAFF/BLyS/TNFSF1 3B
C1q R1/CD93
CCL2/JE/MCP-1
CCL3/CCL4 MIP-1 alpha/beta TABLE 10-continued List of 111 factors participating in the antibody array screen
performed with plasma from mice receiving anti-PD-1 therapy
Proteome Profiler Mouse XL Cytokine Array ™
(R&D Systems; Cat no: ARY028)

CCL5/RANTES
CCL6/C10
CCL11/Eotaxin
CCL12/MCP-5
CCL17/TARC
CCL19/MIP-3 beta
CCL20/MIP-3 alpha
CCL21/6Ckine
CCL22/MDC
CD14
CD40/TNFRSF5
CD160
Chemerin
Chitinase 3-like 1
Coagulation Factor III/Tissue Factor
Complement Component C5/C5a
Complement Factor D
C-Reactive Protein/CRP
CX3CL1/Fractalkine
CXCL1/KC
CXCL2/MIP-2
CXCL9/MIG
CXCL10/IP-10
CXCL11/I-TAC
CXCL13/BLC/BCA-1
CXCL16
Cystatin C
Dkk-1
DPPIV/CD26
EGF
Endoglin/CD105
Endostatin
Fetuin A/AHSG
FGF acidic
FGF-21
Flt-3 Ligand
Gas6
G-CSF
GDF-15
GM-CSF
HGF
ICAM-1/CD54
IFN-gamma
IGFBP-1
IGFBP-2
IGFBP-3
IGFBP-5
IGFBP-6
IL-1 alpha/IL1F1
IL-1 beta/IL-1F2
IL-1ra/IL-1F3
IL-2
IL-3
IL-4
IL-5
IL-6
IL-7
IL-10
IL-11
IL-12p40
IL-13
IL-15
IL-17A
IL-22
IL-23
IL-27
IL-28
IL-33
LDL R
Leptin
LIF
Lipocalin-2/NGAL
LIX
M-CSF
MMP-2
MMP-3
MMP-9
Myeloperoxidase
Osteopontin (OPN)
Osteoprotegerin/TNF RSF11B
PD-ECGF/Thymidine phosphorylase
PDGF-BB
Pentraxin 2/SAP
Pentraxin 3/TSG-14
Periostin/OSF-2
Pref-1/DLK-1/FA1
Proliferin
Proprotein Convertase 9/PCSK9
RAGE
RBP4
Reg3G
Resistin
E-Selectin/CD62E
P-Selectin/CD62P
Serpin E1/PAI-1
Serpin F1/PEDF
Thrombopoietin
TIM-1/KIM-1/HAVCR
TNF-alpha
VCAM-1/CD106
VEGF
WISP-1/CCN4

TABLE 11

Summary of fold changes in the levels of circulating
factors in anti-PD1-treated vs control BALB/c mice

| | Fold change (anti-PD-1 vs IgG) |
|---|---|
| C14 | 8.0 |
| CCL17/TARC | 5.0 |
| CCL19/MIP-3β | 1.5 |
| CCL21/6Ckine | 1.7 |
| CCL3/CCL4/MIP-1α/β | 1.8 |
| CCL5/RANTES | 13.0 |
| CD40/TNFRSF5 | 3.3 |
| Chemerin | 3.6 |
| Chitinase 3-like 1 | 2.6 |
| CXCL13/BCL/BCA-1 | 1.8 |
| CXCL9/MIG | 1.7 |
| Cystatin C | 21.2 |
| DKK-1 | 5.2 |
| Endoglin/CD105 | 2.8 |
| E-Selectin/CD62E | 1.6 |
| Fetuin A/AHSG | 14.6 |
| FGF acidic | 1.7 |
| FGF-21 | 2.5 |
| Gas 6 | 2.1 |
| G-CSF | 2.9 |
| GM-CSF | 2.2 |
| HGF | 3.9 |
| IFN-γ | 1.9 |
| IL-10 | 7.2 |
| IL-12 p40 | 23.5 |
| IL-13 | 2.5 |
| IL-1rα/IL-1F3 | 3.1 |
| IL-2 | 5.5 |
| IL-22 | 2.4 |
| IL-27 p28 | 2.3 |
| IL-28A/B | 2.0 |
| IL-33 | 3.0 |
| IL-4 | 1.5 |
| IL-6 | 15.6 |
| IL-7 | 5.2 |
| LDL R | 8.1 |

TABLE 11-continued

Summary of fold changes in the levels of circulating factors in anti-PD1-treated vs control BALB/c mice

|  | Fold change (anti-PD-1 vs IgG) |
|---|---|
| Leptin | 2.0 |
| LIF | 1.8 |
| Lipocalin-2/NGAL | 4.8 |
| M-CSF | 6.9 |
| MMP-9 | 5.4 |
| Myeloperoxidase | 6.7 |
| Osteprotegerin/TNFRS11B | 1.8 |
| PDGF-BB | 4.1 |
| Pentraxin 2/SAP | 2.7 |
| Pentraxin 3/TSG-14 | 3.3 |
| Periostin/TSG-14 | 2.0 |
| Pref-1/DLK-1/FA1 | 5.8 |
| Proliferin | 5.8 |
| RBP4 | 4.5 |
| Serpin E1/PAI-1 | 3.8 |
| Serpin F1/PAI-1 | 1.6 |
| TIM-1/KIM-1/HAVCR | 1.7 |
| TNF-α | 4.3 |
| VCAM-1/CD106 | 1.6 |
| VEGF | 0.3 |
| WISP-1/CCN4 | 3.0 |

TABLE 12

List of 200 factors participating in the antibody array screen performed with plasma from mice receiving immune-checkpoint inhibitor (anti-PD-1 or anti-PD-L1) therapy Quantibody Mouse Cytokine Array ™ (RayBiotech; Cat no: QAM-CAA-4000)

4-1BB (TNFRSF9/CD137); 6Ckine (CCL21); ACE; Activin A; ADAMTS1 (METH1); Adiponectin; ALK-1; Amphiregulin; ANG-3; ANGPTL3; Artemin; Axl; B7-1; BAFF R; bFGF; BLC (CXCL13); BTC; C5a; CCL28; CCL6; CD27; CD27L; CD30; CD30L; CD36; CD40; CD40L; CD48; CD6; Chemerin; Chordin; Clusterin; CRP; Cardiotrophin-1; CTLA4; CXCL16; Cystatin C; DAN; Decorin; Dkk-1; DLL4; Dtk; E-Cadherin; EDAR; EGF; Endocan; Endoglin; Eotaxin (CCL11); Eotaxin-2 (CCL24); Epigen; Epiregulin; E-selectin; Fas; Fas L; Fcg RIIB; Fetuin A; Flt-3L; Fractalkine; Galectin-1; Galectin-3; Galectin-7; Gas 1; Gas 6; G-CSF; GITR; GITR L; GM-CSF; gp130; Granzyme B; Gremlin; H60; HAI-1; HGF; HGF R; ICAM-1; INFg; IFNg R1; IGF-1; IGFBP-2; IGFBP-3; IGFBP-5; IGFBP-6; IL-1 R4; IL-10; IL-12p40; IL-12p70; IL-13; IL-15; IL-17; IL-17B; IL-17B R; IL-17E; IL-17F; IL-1a; IL-1b; IL-1ra; IL-2; IL-2 Ra; IL-20; IL-21; IL-22; IL-23; IL-28; IL-3; IL-3 Rb; IL-33; IL-4; IL-5; IL-6; IL-7; IL-7 Ra; IL-9; I-TAC (CXCL11); JAM-A; KC (CXCL1); Kremen-1; Leptin; Leptin R; Limitin; Lipocalin-2; LIX; LOX-1; L-selectin; Lungkine; Lymphotactin; MadCAM-1; Marapsin; MBL-2; MCP-1 (CCL2); MCP-5; MCSF; MDC (CCL22); Meteorin; MFG-E8; MIG (CXCL9); MIP-1a (CCL3); MIP-1b (CCL4); MIP-1g; MIP-2; MIP-3a (CCL20); MIP-3b (CCL19); MMP-10; MMP-2; MMP-3; Neprilysin; Nope; NOV; OPG; OPN; Osteoactivin; OX40 Ligand; P-Cadherin; PDGF-AA; Pentraxin 3; Periostin; Persephin; PF4 (CXCL4); PIGF-2; Progranulin; Prolactin; Pro-MMP-9; Prostasin; P-selectin; RAGE; RANTES (CCL5); Renin 1; Resistin; SCF; SDF-1a; sFRP-3; Shh-N; SLAM; TACI; TARC (CCL17); TCA-3; TCK-1 (CXCL7); TECK (CCL25); Testican 3; TGFb1; TIM-1; TNF RI; TNF RII; TNFa; TPO; TRAIL; TRANCE; TREM-1; TREML1; TROY; Tryptase epsilon; TSLP; TWEAK; TWEAK R; VACM-1; VEGF; VEGF R1; VEGF R2; VEGF R3; VEGF-B; VEGF-D

TABLE 13

Summary of fold changes in the levels of circulating factors in anti-PD-L1-treated vs control BALB/c and C57bl/6 mice

| | Fold change (anti-PD-L1 vs IgG) | | | |
|---|---|---|---|---|
| | BALB/c | | C57bl/6 | |
| | Female | Male | Female | Male |
| ADAMTS1 | 1.6 | 0.5 | 2.1 | 1.9 |
| ALK-1 | 2.3 | 1.5 | 6.0 | 0.6 |
| Amphiregulin | 2.7 | 2.8 | 3.0 | 0.9 |
| Axl | 2.7 | 2.2 | 2.3 | 1.9 |
| CD30 | 2.4 | 2.3 | 1.5 | 1.5 |
| Dkk-1 | 1.5 | 0.8 | 1.4 | 0.4 |
| EGF | 6.3 | 4.1 | 0.7 | 4.0 |
| Eotaxin-2 | 1.8 | 1.7 | 1.0 | 0.8 |
| Epiregulin | 2.7 | 0.6 | 0.4 | 0.2 |
| Fcg RIIB | 2.3 | 1.5 | 1.4 | 0.9 |
| Fractalkine | 2.7 | 2.0 | 1.0 | 1.0 |
| G-CSF | 2.2 | 2.7 | 2.0 | 1.2 |
| GITR L | 8.2 | 7.4 | 1.4 | 0.3 |
| Granzyme B | 2.0 | 1.1 | 2.7 | 0.7 |
| HGF | 2.3 | 0.6 | 3.7 | 3.6 |
| HGF R | 10.4 | 1.7 | 24.9 | 2.4 |
| IL-1ra | 3.6 | 1.8 | 2.9 | 1.3 |
| IL-33 | 1.3 | 2.2 | 1.6 | 1.0 |
| IL-6 | 1.8 | 1.7 | 1.0 | 0.5 |
| IL-7 | 1.7 | 1.6 | 1.1 | 0.0 |
| I-TAC | 6.1 | 7.4 | 4.2 | 1.1 |
| Lipocalin-2 | 2.0 | 4.8 | 2.6 | 2.1 |
| MadCAM-1 | 0.8 | 7.1 | 2.6 | 2.4 |
| MCP-5 | 2.2 | 4.5 | 1.3 | 1.2 |
| MDC | 2.2 | 1.8 | 0.9 | 0.6 |
| Meteorin | 0.6 | 0.7 | 1.9 | 3.0 |
| MFG-E8 | 1.8 | 2.6 | 4.3 | 1.8 |
| MIG | 1.6 | 1.2 | 1.9 | 1.4 |
| MIP-3b | 1.5 | 2.8 | 1.7 | 0.9 |

TABLE 13-continued

Summary of fold changes in the levels of circulating factors in anti-PD-L1-treated vs control BALB/c and C57bl/6 mice

| | Fold change (anti-PD-L1 vs IgG) | | | |
|---|---|---|---|---|
| | BALB/c | | C57bl/6 | |
| | Female | Male | Female | Male |
| OPG | 0.8 | 0.9 | 1.7 | 2.2 |
| Osteoactivin | 0.8 | 1.2 | 2.5 | 2.4 |
| P-Cadherin | 0.8 | 0.9 | 1.7 | 2.1 |
| Pentraxin 3 | 1.3 | 1.6 | 3.0 | 2.7 |
| Pro-MMP-9 | 3.0 | 2.2 | 1.1 | 1.3 |
| SCF | 2.6 | 3.3 | 4.5 | 3.4 |
| TACI | 2.7 | 2.9 | 2.3 | 1.3 |
| TARC | 1.4 | 1.6 | 1.5 | 0.5 |
| TNF RII | 1.3 | 2.0 | 1.6 | 2.6 |
| TREM-1 | 2.8 | 1.9 | 7.2 | 3.1 |
| TROY | 2.3 | 1.7 | 6.7 | 6.1 |
| VEGF R1 | 1.9 | 1.3 | 1.8 | 0.3 |

TABLE 14

Summary of fold changes in the levels of circulating factors in anti-PD1-treated vs control BALB/c and SCID mice

| | Fold change (anti-PD-1 vs IgG) | |
|---|---|---|
| | BALB/c | SCID |
| ADAMTS1 | 2.4 | 0.3 |
| ALK-1 | 3.4 | 3.4 |
| Amphiregulin | 3.7 | 0.0 |
| CD40L | 3.6 | 0.9 |
| Dkk-1 | 2.0 | 0.8 |
| Epigen | 2.3 | 1.8 |
| IL-17B | 3.4 | 0.3 |
| IL-17B R | 2.1 | 0.9 |
| IL-1ra | 8.7 | 1.5 |
| IL-21 | 2.6 | 1.0 |
| IL-22 | 9.1 | 0.0 |
| IL-6 | 2.1 | 1.8 |
| I-TAC | 9.3 | 1.1 |
| MFG-E8 | 2.8 | 0.6 |
| Osteoactivin | 2.5 | 2.0 |
| SCF | 2.0 | 0.0 |
| TARC | 1.5 | 0.9 |
| TREM-1 | 3.9 | 0.3 |
| TROY | 1.7 | 0.7 |
| VEGF R1 | 2.6 | 0.8 |

TABLE 15

Patients' characteristics

| Characteristics | Colorectal patients N = 17 |
|---|---|
| Sex, n (%) | |
| Female | 8 (47) |
| Male | 9 (53) |
| Age, mean (range) | 59.6 (41-79) |
| Stage, n (%) | |
| I-III | 13 (76) |
| IV | 4 (24) |

REFERENCES

Alishekevitz D, Gingis-Velitski, Svetlana, Kaidr-Person, Orit, Gutter-Kapon, Lilach, D. Scherer, Sandra, Raviv, Ziv, Merquiol, Emmanuelle, Ben-Nun, Yael, Miller, Valeria, Rachman-Tzemah, Chen, Timaner, Michael, Mumblat, Yelena, Ilan, Neta, Loven, David, Hershkovitz, Dov, Satch-Fainaro, Ronit, Blum, Galia, Sleeman, Jonathan, Vlodavsky, Israel, Shaked, Yuval. Macrophage-induced Lymphangiogenesis and Metastasis following Paclitaxel Chemotherapy is Regulated by VEGFR3 Cell Rep 2016 Oct. 25; 17(5): 1344-1356.doi:10.1016/j.celrep.2016.09.083

Beyar-Katz O, Magidey K, Ben-Tsedek N, Alishekevitz D, Timaner M, Miller V, Lindzen M, Yarden Y, Avivi I, Shaked Y. Bortezomib-induced proinflammatory macrophages as a potential factor limiting anti-tumour efficacy. J Pathol. 2016 Vol. 239, Issue 3. Version on line: 29 Apr. 2016/DOI:10.1002/path.4723.

Chen C S, Doloff J C, Waxman D J. Intermittent metronomic drug schedule is essential for activating antitumor innate immunity and tumor xenograft regression. Neoplasia. 2014 16(1):84-96

De Henau O, Rausch M, Winkler D, Campesato L F, Liu C, Cymerman D H, Budhu S, Ghosh A, Pink M, Tchaicha J, Douglas M, Tibbitts T, Sharma S, Proctor J, Kosmider N, White K, Stern H, Soglia J, Adams J, Palombella V J, McGovern K, Kutok J L, Wolchok J D, Merghoub T. Overcoming resistance to checkpoint blockade therapy by targeting PI3Kgamma in myeloid cells. Nature. 2016; 539(7629):443-7.

De Palma M, Lewis C E. Macrophage regulation of tumor responses to anticancer therapies. Cancer Cell. 2013; 23(3):277-86.

Doloff J C, Waxman D J. VEGF receptor inhibitors block the ability of metronomically dosed cyclophosphamide to activate innate immunity-induced tumor regression. Cancer Res. 2012; 72(5):1103-15.

Duraiswamy J, Kaluza K M, Freeman G J, Coukos G. Dual blockade of PD-1 and CTLA-4 combined with tumor vaccine effectively restores T-cell rejection function in tumors. Cancer Res. 2013; 73(12):3591-603.

Gajewski T F, Schreiber H, Fu Y X. Innate and adaptive immune cells in the tumor microenvironment. Nat Immunol. 2013; 14(10):1014-22.

Giesen C, Wang H A, Schapiro D, Zivanovic N, Jacobs A, Hattendorf B, Schuffler P J, Grolimund D, Buhmann J M, Brandt S, Varga Z, Wild P J, Gunther D, Bodenmiller B. Highly multiplexed imaging of tumor tissues with subcellular resolution by mass cytometry. Nat Methods. 2014; 11(4):417-22.

Gingis-Velitski S, Loven D, Benayoun L, Munster M, Bril R, Voloshin T, Alishekevitz D, Bertolini F, Shaked Y. Host response to short-term, single-agent chemotherapy induces matrix metalloproteinase-9 expression and accelerates metastasis in mice. Cancer Res. 2011; 71(22):6986-96.

Hughes C S, Postovit L M, Lajoie G A. Matrigel: a complex protein mixture required for optimal growth of cell culture. Proteomics. 2010; 10(9):1886-90.

Katz O B, Shaked Y. Host effects contributing to cancer therapy resistance. Drug Resist Updat. 2015; 19:33-42.

Kim K H, Sederstrom J M. Assaying Cell Cycle Status Using Flow Cytometry. Current protocols in molecular biology. 2015; 111:28 6 1-11.

Kim J, Denu R A, Dollar B A, Escalante L E, Kuether J P, Callander N S, Asimakopoulos F, Hematti P. Macrophages and mesenchymal stromal cells support survival and proliferation of multiple myeloma cells. British Journal of Haematology. 2012; 158(3):336-46.

Kodumudi K N, Siegel J, Weber A M, Scott E, Sarnaik A A, Pilon-Thomas S. Immune Checkpoint Blockade to Improve Tumor Infiltrating Lymphocytes for Adoptive Cell Therapy. PloS one. 2016; 11(4):e0153053.

Kruisbeek A M. In vivo depletion of CD4- and CD8-specific T cells. Curr Protoc Immunol. 2001; Chapter 4:Unit 4 1.

Ma Y, Adjemian S, Mattarollo S R, Yamazaki T, Aymeric L, Yang H, Portela Catani J P, Hannani D, Duret H, Steegh K, Martins I, Schlemmer F, Michaud M, Kepp O, Sukkurwala A Q, Menger L, Vacchelli E, Droin N, Galluzzi L, Krzysiek R, Gordon S, Taylor P R, Van Endert P, Solary E, Smyth M J, Zitvogel L, Kroemer G. Anticancer chemotherapy-induced intratumoral recruitment and differentiation of antigen-presenting cells. Immunity. 2013; 38(4):729-41.

Makkouk A, Weiner G J. Cancer immunotherapy and breaking immune tolerance: new approaches to an old challenge. Cancer Res. 2015; 75(1):5-10.

Ostrand-Rosenberg S, Sinha P. Myeloid-derived suppressor cells: linking inflammation and cancer. Journal of Immunology. 2009; 182(8):4499-506.

Pardoll D M. The blockade of immune checkpoints in cancer immunotherapy. Nature reviews Cancer. 2012; 12(4):252-64.

Postow M A, Callahan M K, Wolchok J D. Immune Checkpoint Blockade in Cancer Therapy. J Clin Oncol. 2015; 33(17):1974-82.

Qiu P, Simonds E F, Bendall S C, Gibbs K D, Jr., Bruggner R V, Linderman M D, Sachs K, Nolan G P, Plevritis S K. Extracting a cellular hierarchy from high-dimensional cytometry data with SPADE. Nat Biotechnol. 2011; 29(10):886-91.

Rachman-Tzemah C, Zaffryar-Eilot S, Grossman M, Ribero D, Timaner M, Maki J M, Myllyharju J, Bertolini F, Hershkovitz D, Sagi I, Hasson P, Shaked Y. Blocking Surgically Induced Lysyl Oxidase Activity Reduces the Risk of Lung Metastases. Cell Reports. 2017; 19(4):774-84

Ran F A, Hsu P D, Lin C Y, Gootenberg J S, Konermann S, Trevino A E, Scott D A, Inoue A, Matoba S, Zhang Y, Zhang F. Double nicking by RNA-guided CRISPR Cas9 for enhanced genome editing specificity. Cell. 2013; 154 (6):1380-9.

Ran F A, Hsu P D, Wright J, Agarwala V, Scott D A, Zhang F. Genome engineering using the CRISPR-Cas9 system. Nat Protoc. 2013; 8(11):2281-308.

Romano E, Romero P. The therapeutic promise of disrupting the PD-1/P D-L1 immune checkpoint in cancer: unleashing the CD8 T cell mediated anti-tumor activity results in significant, unprecedented clinical efficacy in various solid tumors. J Immunother Cancer. 2015; 3:15.

Sato T, Terai M, Tamura Y, Alexeev V, Mastrangelo M J, Selvan S R. Interleukin 10 in the tumor microenvironment: a target for anticancer immunotherapy. Immunol Res. 2011; 51(2-3):170-82.

Shaked Y. Balancing efficacy of and host immune responses to cancer therapy: the yin and yang effects. Nat Rev Clin Oncol. 2016.

Shaked Y, Kerbel R S. Antiangiogenic strategies on defense: on the possibility of blocking rebounds by the tumor vasculature after chemotherapy. Cancer Res. 2007; 67(15):7055-8.

Shaked Y, Ciarrocchi A, Franco M, Lee C R, Man S, Cheung A M, Hicklin D J, Chaplin D, Foster F S, Benezra R, Kerbel R S. Therapy-induced acute recruitment of circulating endothelial progenitor cells to tumors. Science. 2006; 313(5794):1785-7.

Shaked Y, Henke E, Roodhart J M, Mancuso P, Langenberg M H, Colleoni M, Daenen L G, Man S, Xu P, Emmenegger U, Tang T, Zhu Z, Witte L, Strieter R M, Bertolini F, Voest E E, Benezra R, Kerbel R S. Rapid chemotherapy-induced acute endothelial progenitor cell mobilization: implications for antiangiogenic drugs as chemosensitizing agents. Cancer Cell. 2008; 14(3):263-73.

Sharma P, Hu-Lieskovan S, Wargo J A, Ribas A. Primary, Adaptive, and Acquired Resistance to Cancer Immunotherapy. Cell. 2017; 168(4):707-23.

Swart M, Verbrugge I, Beltman J B. Combination Approaches with Immune-Checkpoint Blockade in Cancer Therapy. Frontiers in Oncology. 2016; 6:233.

Sun Z, Fourcade J, Pagliano O, Chauvin J M, Sander C, Kirkwood J M, Zarour H M. IL10 and PD-1 Cooperate to Limit the Activity of Tumor-Specific CD8+ T Cells. Cancer Res. 2015; 75(8):1635-44.

Timaner M, Beyar-Katz O, Shaked Y. Analysis of the Stromal Cellular Components of the Solid Tumor Microenvironment Using Flow Cytometry. Curr Protoc Cell Biol. 2016; 70:19 81-82.

Topalian S L, Drake C G, Pardoll D M. Immune checkpoint blockade: a common denominator approach to Cancer Immunotherapy. Cancer Cell 2015; 27(4): 450-61.

The invention claimed is:

1. A method of treating a colon cancer patient with radiotherapy, the method comprising the steps of:
   (i) calculating a fold change in Interleukin 7 (IL-7) protein expression produced by said colon cancer patient in response to treatment with said radiotherapy in blood samples obtained from said cancer patient before a first treatment with said radiotherapy and after said first treatment with said radiotherapy, wherein said blood sample is selected from the group consisting of blood plasma, whole blood, blood serum and peripheral blood mononuclear cells; wherein an increase in protein expression from before said first treatment to after said first treatment of IL-7 indicates a colon cancer patient with a non-favorable response to said treatment with said radiotherapy; and
   (ii) treating said patient with a non-favorable response with an antibody that binds to IL-7 receptor (IL-7R) and blocks its activity, in combination with a second treatment with said radiotherapy.

2. The method of claim 1, wherein the blood samples before and after said first treatment are both blood plasma.

3. The method of claim 1, wherein said increase comprises a fold-change of 1.5 or higher.

4. The method of claim 1, wherein the cancer is a primary or a metastatic cancer.

5. The method of claim 1, wherein said after said first treatment with said radiotherapy is at least 24 hours after said first treatment and wherein said before said first treatment with said radiotherapy is at most 72 hours before said first treatment.

6. The method of claim 1, wherein the second treatment with said radiotherapy and the antibody are administered concurrently or sequentially, in either order.

7. A method for treatment of a colon cancer patient non-responsive to treatment with radiotherapy, the method comprising administering to the cancer patient an antibody that binds to IL-7R and blocks its activity, in combination with a second treatment with said radiotherapy, wherein said colon cancer patient is confirmed as having an increased IL-7 protein expression in a blood sample obtained from said colon cancer patient after administration of a first treatment with said radiotherapy as compared to a blood sample obtained from said colon cancer patient before administration of said first treatment with said radiotherapy, wherein said blood sample is selected from the group consisting of blood plasma, whole blood, blood serum and peripheral blood mononuclear cells.

8. The method of claim 7, wherein said colon cancer patient is confirmed as having an increased IL-6 protein expression in a blood sample obtained from said colon cancer patient after administration of said first treatment with said radiotherapy as compared to a blood sample obtained from said colon cancer patient before administration of said first treatment with said radiotherapy.

9. The method of claim 7, wherein the cancer is a primary or a metastatic cancer.

10. The method of claim 7, wherein the blood samples before and after said first treatment are both blood plasma.

11. The method of claim 7, wherein said increase comprises a fold-change of 1.5 or higher.

12. The method of claim 7, wherein said after said first treatment with said radiotherapy is at least 24 hours after said first treatment and wherein said before said first treatment with said radiotherapy is at most 72 hours before said first treatment.

13. The method of claim 7, wherein the second treatment with said radiotherapy and the antibody are administered concurrently or sequentially, in either order.

14. A method of treating a colon cancer patient with radiotherapy, the method comprising the steps of:

(i) calculating a fold change in Interleukin 7 (IL-7) protein expression produced by said colon cancer patient in response to treatment with said radiotherapy in blood samples obtained from said cancer patient before a first treatment with said radiotherapy and after said first treatment with said radiotherapy, wherein said blood sample is selected from the group consisting of blood plasma, whole blood, blood serum and peripheral blood mononuclear cells; wherein an increase in protein expression from before said first treatment to after said first treatment of IL-7 indicates a colon cancer patient with a non-favorable response to said treatment with said radiotherapy; and (ii) treating said patient with a non-favorable response with an antibody that binds to IL-7 receptor (IL-7R) and blocks its activity, in combination with a second treatment with said radiotherapy, wherein an amount of said antibody effective to increase the therapeutic efficacy of said second treatment with said radiotherapy is administered.

* * * * *